US012639647B2

(12) United States Patent
  Safari

(10) Patent No.: US 12,639,647 B2
(45) Date of Patent: May 26, 2026

(54) SYSTEM AND METHOD FOR IDENTIFYING AND ENFORCING THE USE OF SAFE CLEANING PRODUCTS AND CHEMICAL FOR CLEANING OF A BUILDING

(71) Applicant: GIGO Clean Technology Inc., Santa Ana, CA (US)

(72) Inventor: Bita Safari, Santa Ana, CA (US)

(73) Assignee: GIGO Clean Technology Inc., Santa Ana, CA (US)

( * ) Notice: Subject to any disclaimer, the term of this patent is extended or adjusted under 35 U.S.C. 154(b) by 209 days.

(21) Appl. No.: 18/401,699

(22) Filed: Jan. 1, 2024

(65) Prior Publication Data

US 2024/0220885 A1    Jul. 4, 2024

Related U.S. Application Data

(60) Provisional application No. 63/436,327, filed on Dec. 30, 2022.

(51) Int. Cl.
  *G06Q 10/00*       (2026.01)
  *G06Q 10/0631*      (2023.01)
  *G16C 20/00*       (2019.01)
  *G16C 20/20*       (2019.01)

(52) U.S. Cl.
  CPC ..... *G06Q 10/063118* (2013.01); *G16C 20/20* (2019.02)

(58) Field of Classification Search
  None
  See application file for complete search history.

(56) References Cited

U.S. PATENT DOCUMENTS

| | | | |
|---|---|---|---|
| 7,236,976 B2 | 6/2007 | Breitenbach et al. | |
| 7,782,713 B2 | 8/2010 | Talarico | |
| 9,813,992 B2 * | 11/2017 | Peinhardt | G01S 5/0036 |
| 10,664,673 B2 | 5/2020 | Schenk et al. | |
| 2008/0288279 A1 | 11/2008 | Hanley et al. | |

(Continued)

OTHER PUBLICATIONS

Chai PR, Zhang H, Jambaulikar GD, Boyer EW, Shrestha L, Kitmitto L, Wickner PG, Salmasian H, Landman AB An Internet of Things Buttons to Measure and Respond to Restroom Cleanliness in a Hospital Setting: Descriptive Study J Med Internet Res 2019;21(6):e13588 (Year: 2019).*

*Primary Examiner* — Matheus Ribeiro Stivaletti
(74) *Attorney, Agent, or Firm* — Makoui Law, PC; Ali Makoui

(57)        ABSTRACT

A method of identifying the cleaning products and chemicals that are safe for a particular cleaning task and ensuring that the cleaning workers carry the identified cleaning products and chemicals to a cleaning job site. The cleaning workers are requested to activate geotagging and location sharing on their client devices. When the client device reaches within a threshold distance of a job site, the cleaning worker is requested to activate the camera of the client device and take geotagged images of the cleaning products that the cleaning worker is carrying. The images of the cleaning products are analyzed and are compared with the products and chemicals that are identified as being safe for the cleaning job. The cleaning worker gets clearance to perform the cleaning job only after the cleaning products that are actually carried to the job site and their chemical ingredients are verified as safe.

20 Claims, 17 Drawing Sheets

(56) References Cited

U.S. PATENT DOCUMENTS

| | | | |
|---|---|---|---|
| 2010/0274640 A1* | 10/2010 | Morey .................... | B08B 13/00 |
| | | | 709/224 |
| 2012/0306645 A1 | 12/2012 | Sarna, II | |
| 2014/0032382 A1 | 1/2014 | Hamann et al. | |
| 2014/0156412 A1* | 6/2014 | Tse ......................... | G06Q 50/01 |
| | | | 705/14.58 |
| 2019/0304330 A1 | 10/2019 | Schenk et al. | |
| 2020/0250774 A1* | 8/2020 | Agarwal .......... | G06Q 10/06315 |

\* cited by examiner

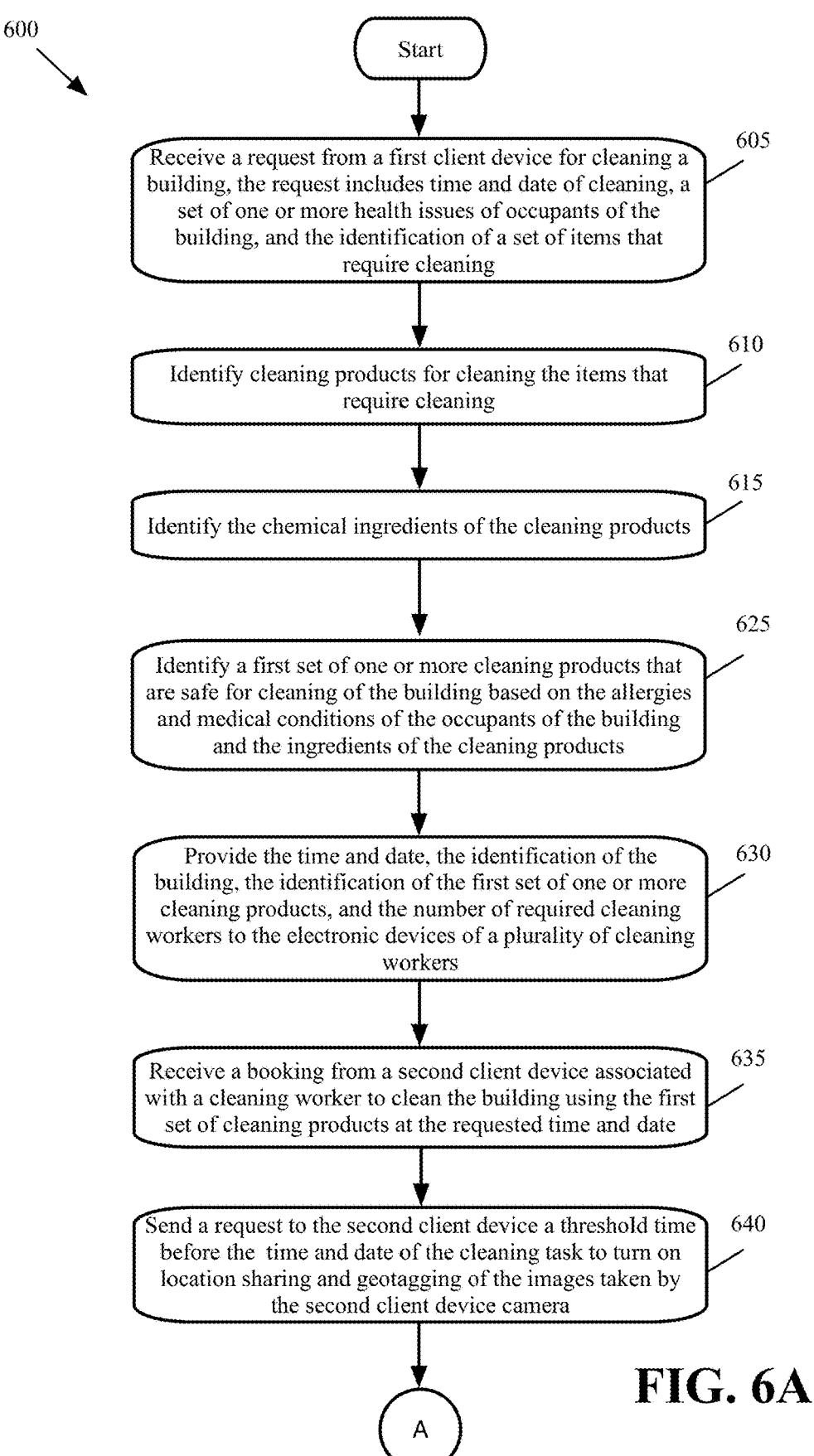

600

Start

605
Receive a request from a first client device for cleaning a building, the request includes time and date of cleaning, a set of one or more health issues of occupants of the building, and the identification of a set of items that require cleaning 610
Identify cleaning products for cleaning the items that require cleaning 615
Identify the chemical ingredients of the cleaning products 625
Identify a first set of one or more cleaning products that are safe for cleaning of the building based on the allergies and medical conditions of the occupants of the building and the ingredients of the cleaning products 630
Provide the time and date, the identification of the building, the identification of the first set of one or more cleaning products, and the number of required cleaning workers to the electronic devices of a plurality of cleaning workers 635
Receive a booking from a second client device associated with a cleaning worker to clean the building using the first set of cleaning products at the requested time and date 640
Send a request to the second client device a threshold time before the time and date of the cleaning task to turn on location sharing and geotagging of the images taken by the second client device camera

SYSTEM AND METHOD FOR IDENTIFYING AND ENFORCING THE USE OF SAFE CLEANING PRODUCTS AND CHEMICAL FOR CLEANING OF A BUILDING

CLAIM OF BENEFIT TO PRIOR APPLICATIONS

This application claims the benefit of U.S. Provisional Patent Application Ser. No. 63/436,327, filed on Dec. 30, 2022. The contents of U.S. Provisional Patent Application 63/436,327 are hereby incorporated by reference.

BACKGROUND

Janitorial services are provided to clean residential areas, offices, and public buildings. A varieties of chemical may be used during a cleaning job to clean and disinfect different surfaces may be made of tiles, glass, granite, marble, brace, nickel, iron, stainless steel, etc. Even though the chemicals may be adequate for a desired cleaning task, they may cause adverse effects on the human or pet occupants of a building.

BRIEF DESCRIPTION OF THE DRAWINGS

The various embodiments of the present system and method for identifying and enforcing the user of safe products and chemical for cleaning of a building now will be discussed in detail with an emphasis on highlighting the advantageous features. These embodiments depict the novel and non-obvious systems and methods shown in the accompanying drawings, which are for illustrative purposes only. These drawings include the following figures, in which like numerals indicate like parts:

FIGS. 6A-6B are a flowchart illustrating an example process for ensuring that cleaning products and their chemical components are safe for a particular cleaning job, according to various aspects of the present disclosure;

2

Figure 7:
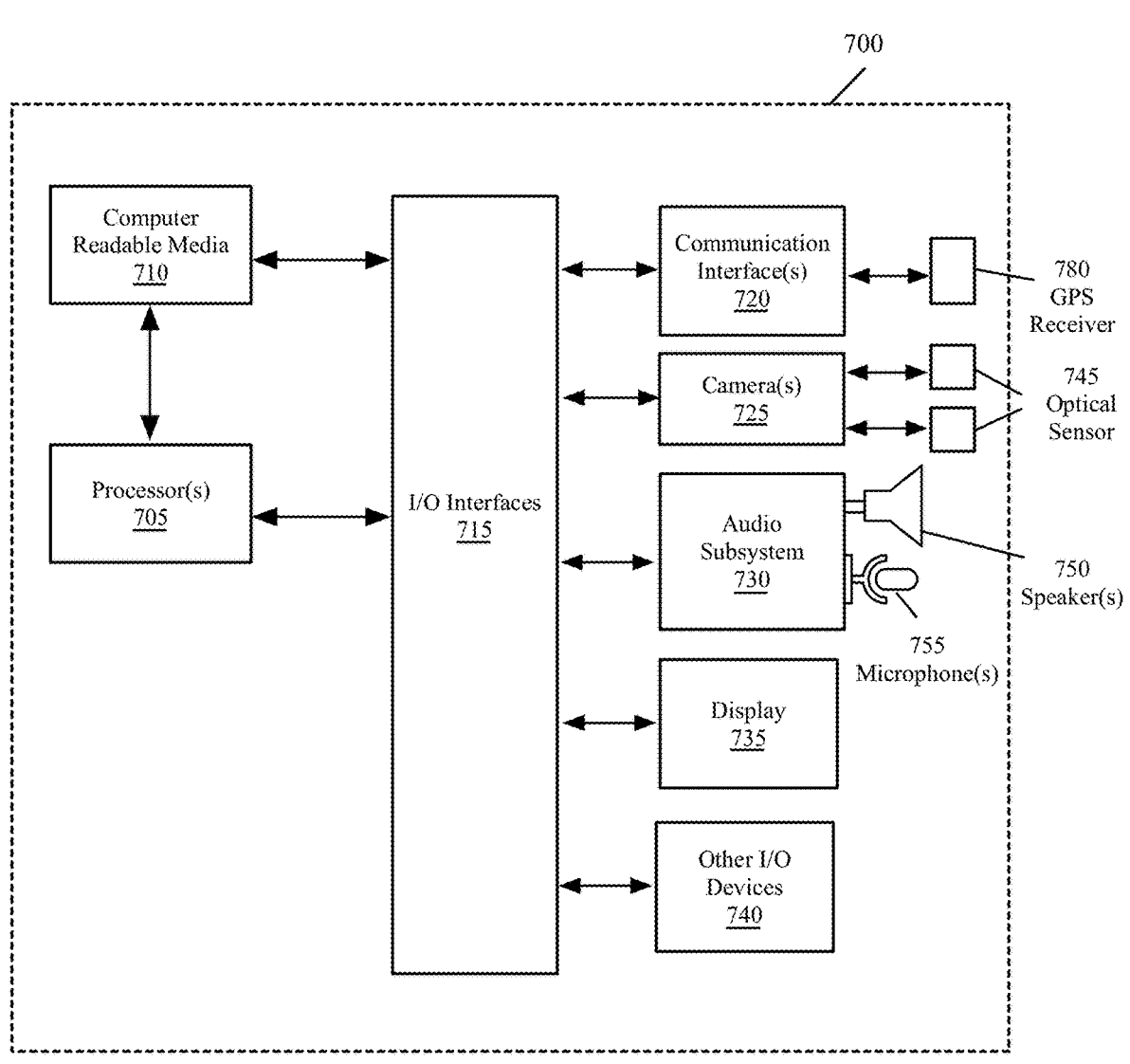
Figure 8:
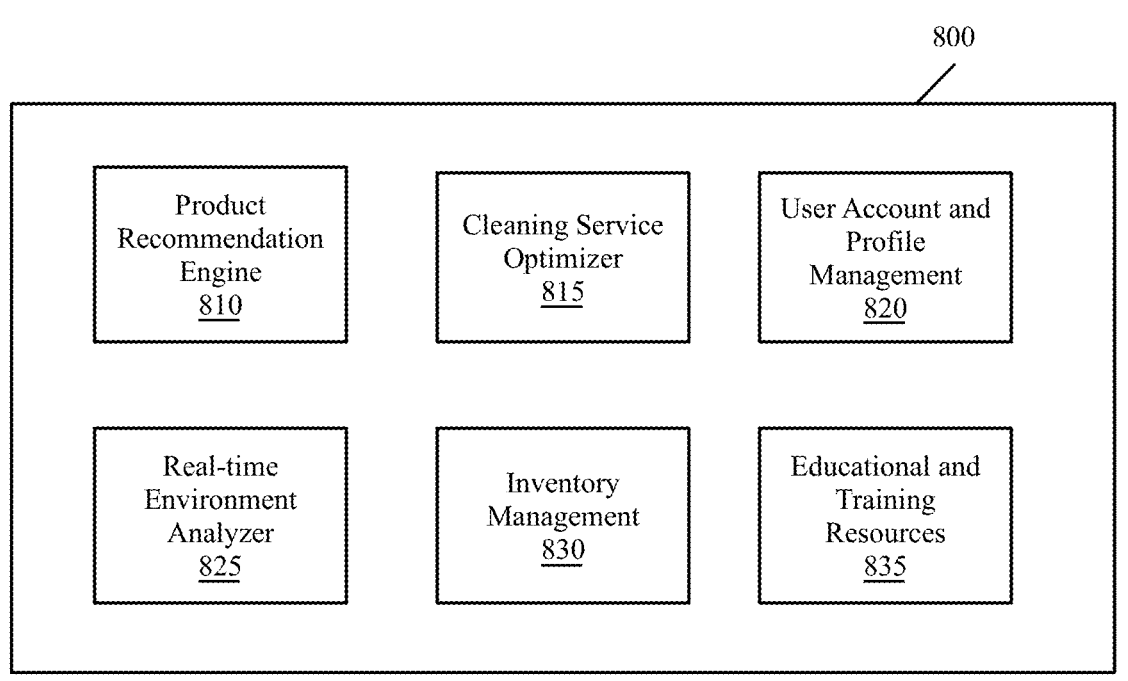
Figure 9:
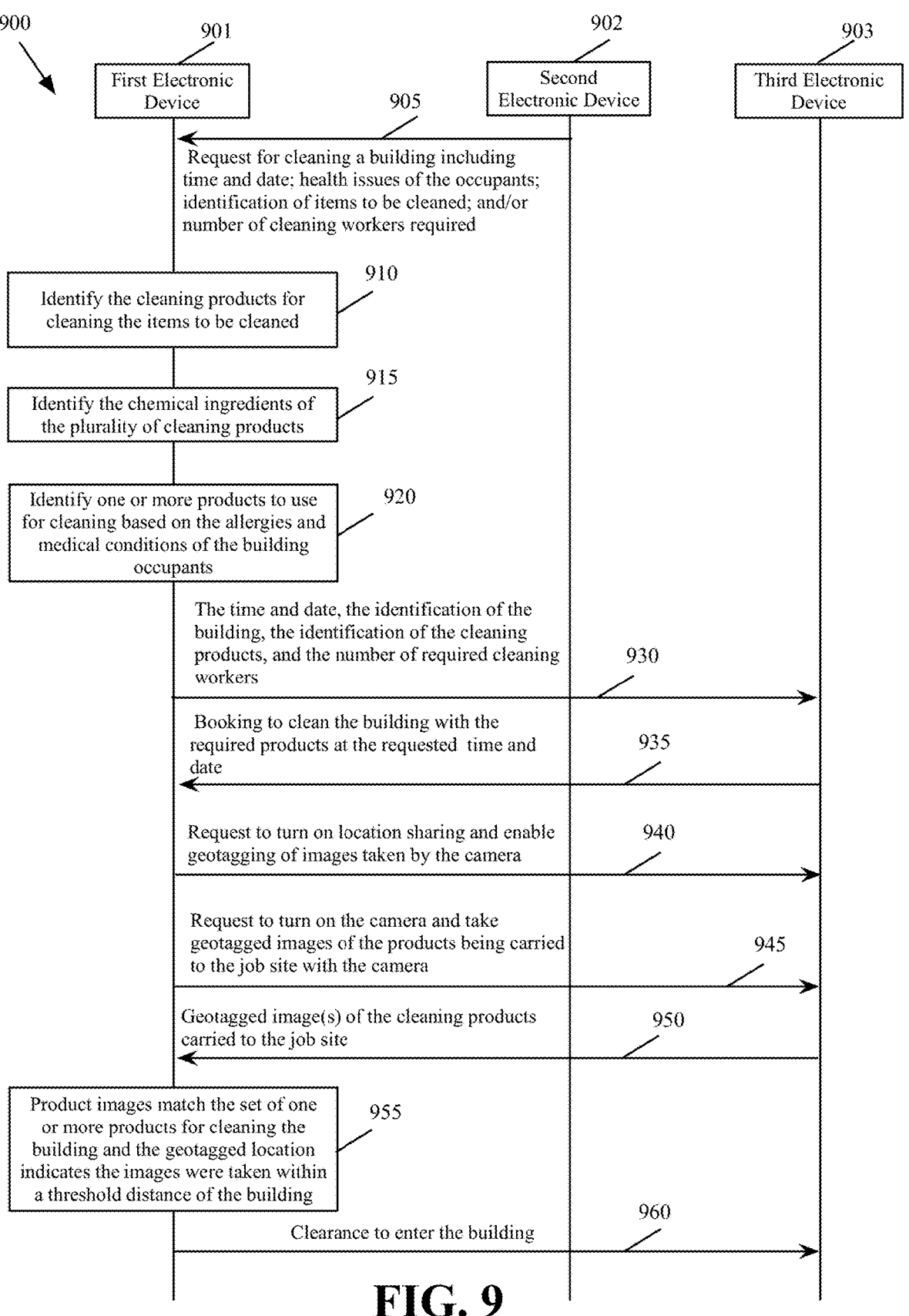
Figure 10:
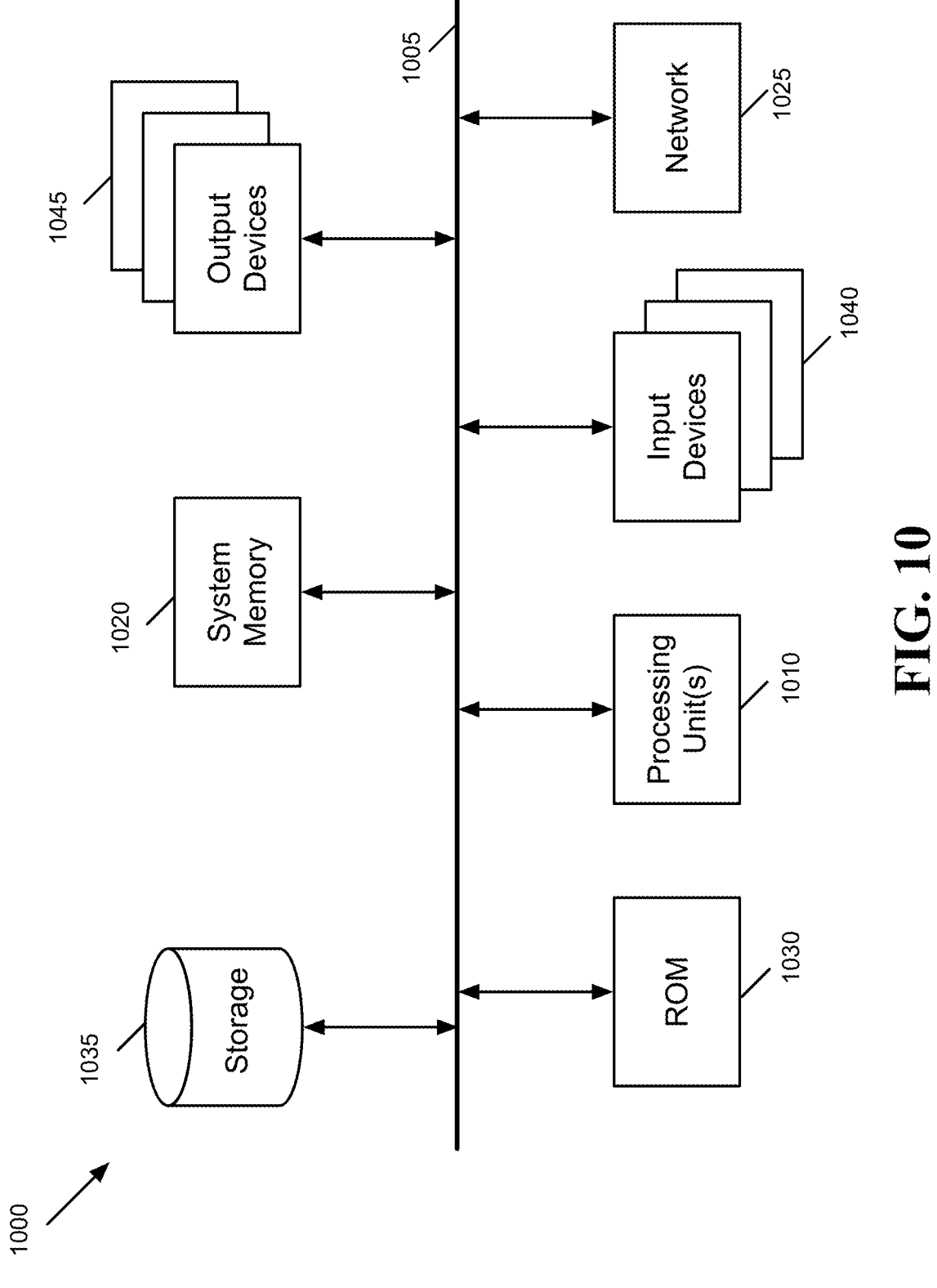

FIG. 7 is a functional diagram illustrating an example architecture of a client device, according to various aspects of the present disclosure;

FIG. 8 is a software block diagram illustrating examples of software components of a janitorial service provider server, according to various aspects of the present disclosure;

FIG. 9 is an example sequence diagram illustrating message flows and operations performed for ensuring that safe cleaning products are selected and carried to a cleaning job site, according to various aspects of the present embodiments; and FIG. 10 conceptually illustrates an electronic system with which some embodiments of the invention are implemented.

DETAILED DESCRIPTION

One aspect of the present embodiments includes the realization that the wide range of chemicals that are used during a cleaning job to clean and disinfect different surfaces that are made of tiles, glass, granite, marble, brace, nickel, iron, stainless steel, etc., may cause adverse effects on the human or pet occupants of a building. The cleaning workers often purchase inexpensive products that may have unsafe chemicals. Even if the products with the proper chemicals are identified, there is no guarantee that the cleaning workers will actually carry and use the identified products at the job site.

Another aspect of the present embodiments includes the realization that surfaces that require cleaning may include large concentration of invisible microbes and bacteria. The cleaning workers may not be able to identify the contaminated surfaces and identify the proper methods and chemicals that are required to clean these surfaces.

The present embodiments, as described in detail below, solve the above-mentioned problems by providing a method and a system that identify the cleaning products and chemicals that are safe for a particular cleaning task and ensure that the cleaning workers carry the cleaning products and chemicals that are identified as safe to a cleaning job site. The cleaning workers may be requested to take geotagged images of the cleaning products that they are carrying when a client device associated with the cleaning workers reach within a threshold distance of a job site. The images of the cleaning products and their chemical ingredients may be analyzed and may be compared with the products and chemicals that are identified as being safe for the cleaning job. The cleaning workers may get clearance to perform the cleaning job only after the cleaning products that are actually carried to the job site and their chemical ingredients of the cleaning products are verified as safe.

The present embodiments may use handheld microbial detection sensors that may detect and measure adenosine triphosphate (ATP) which are found in the living cells. The measurement of ATP may provide a direct measurement of biological concentration on a surface. The results of the measurements may be stored in the profiles of cleaning customers to select proper cleaning products and chemical for furfure cleaning jobs. The results of the measurements may be analyzed to provide instructions to the cleaning workers on a job site to use proper cleaning methods (e.g., deep cleaning), to use proper safety equipment (e.g., to wear breathing masks or gloves), and/or to select proper cleaning products and chemicals from the authorized products cleaning products and chemicals that they have carrier to the job site to clean the contaminated surfaces.

The remaining detailed description describes the present embodiments with reference to the drawings. In the drawings, reference numbers label elements of the present embodiments. These reference numbers are reproduced below in connection with the discussion of the corresponding drawing features.

Figure 1A:
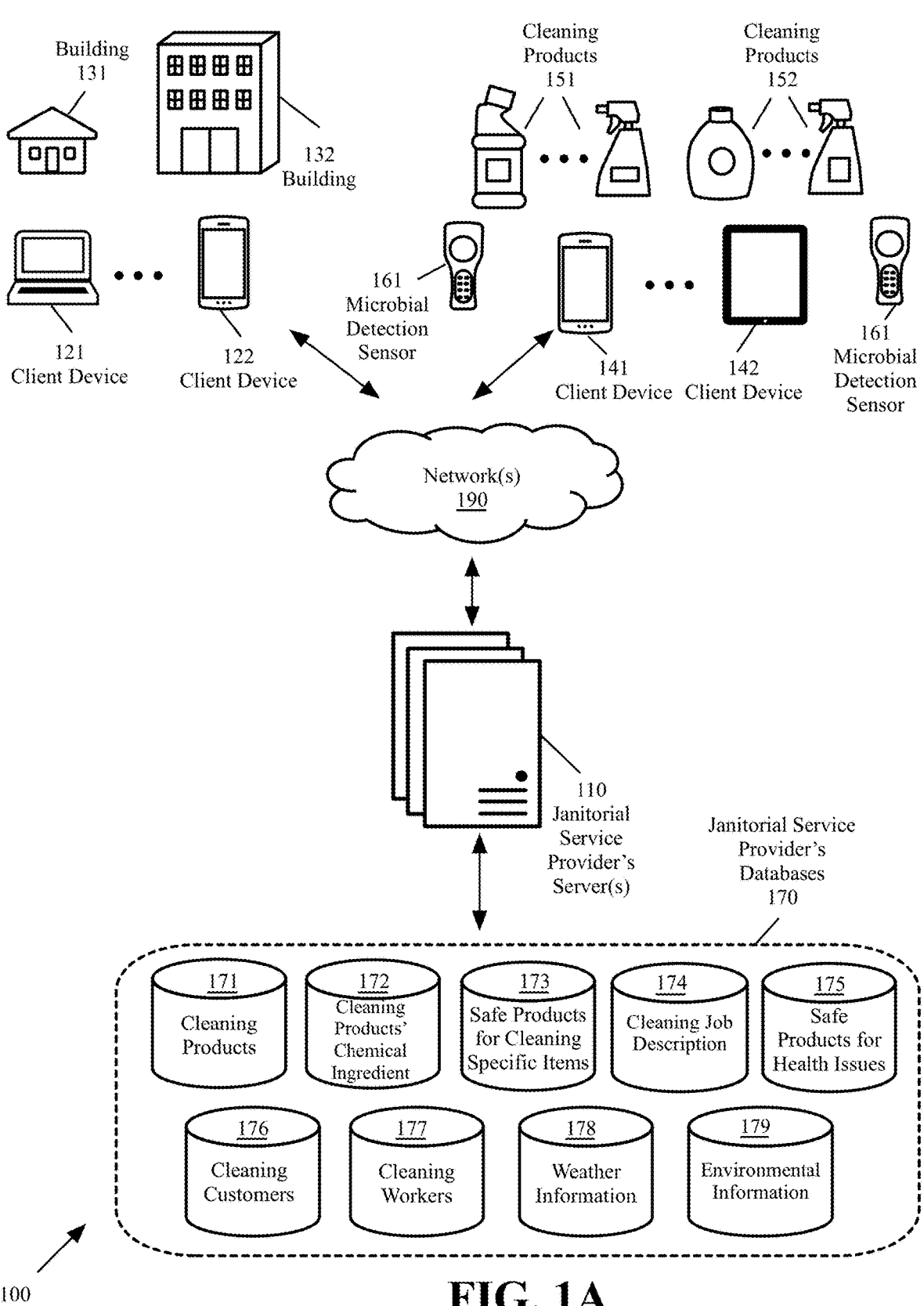
FIG. 1A is a functional diagram illustrating an example embodiment of a system for identifying approved chemicals and ensuring that identified products are carried by the cleaning workers to a job site, according to various aspects of the present disclosure.

FIG. 1A is a functional diagram illustrating an example embodiment of a system 100 for identifying approved chemicals and ensuring that identified products are carried by the cleaning workers to a job site, according to various aspects of the present disclosure. With reference to FIG. 1A, the system 100 may include one or more janitorial service provider's servers 110, several client devices 121-122 associated with properties 131-132 that require cleaning, and several client devices 141-142 associated with cleaning workers.

The janitorial service provider's servers 110 and the client devices 121-122 and 141-142 may communicate with each other through one or more networks 190. The network(s) 190 may be one or more of the Internet, intranets, cellular networks, networks of servers/backend devices, and/or users' networks (e.g., Wi-Fi, Ethernet, etc.).

The janitorial service provider's servers 110 may maintain, or may have access to, the databases 170. The databases 170 may include the cleaning products database 171, the cleaning products' chemical ingredient database 172, the safe products for cleaning specific items database 173, the cleaning job description database 174, the safe products for health issues database 175, the cleaning customers database 176, the cleaning workers database 177, the weather information databases 178, and the environmental information databases 179.

The janitorial service provider's servers 110 may store the cleaning worker's information in a storage, such as, the cleaning workers database 177. The cleaning workers associated with the client devices 141-142 may carry cleaning products, such as, the cleaning products 151-152. The cleaning persons associated with the client devices 141-142 may carry measurement sensors, such as portable microbial detection sensors 161, to measure the level of microbes and bacteria on the job site surfaces, such as kitchen sinks, counter tops, bathtubs, work benches, equipment, etc. Some of the portable microbial detection sensors 161 may measure ATP molecules, which are found in the living cells. The measurement of ATP may provide a direct measurement of biological concentration on a surface. ATP may be quantified by measuring the light produced through its reaction with the naturally occurring enzymes using a photometer that may be included in the microbial detection sensors 161. The amount of light produced may be proportional to the amount of ATP present on the surface.

The results of the measurements may be stored in the profiles of cleaning customers, for example, in the cleaning customers database 176. The results the measurements may be used to select proper cleaning products and chemical for furfure cleaning jobs. The results of the measurements may be analyzed to provide instructions to the cleaning workers on a job site to use proper cleaning methods (e.g., deep cleaning), to use proper safety equipment (e.g., to wear breathing masks or gloves), and/or to select proper cleaning products and chemicals from the authorized products cleaning products and chemicals that they have carrier to the job site to clean the contaminated surfaces.

The cleaning products database 171 may store the identification of different cleaning products available in the market. The cleaning products' chemical ingredient database 172 may store the chemical ingredients of different cleaning products. Some of these cleaning products may have to be avoided for certain cleaning jobs because either one of the occupants had an allergy or medical condition (e.g., as described below in stage 408 of FIG. 4B) that may be aggravated by using those products or the cleaning request may have indicated (e.g., as described below through the option 462 of FIG. 4B) that those cleaning products shall not be used. In addition, some cleaning jobs may include requests for particular cleaning products (e.g., as indicated in the display area 472 in stage 409 of FIG. 4C described below).

Figure 1B:
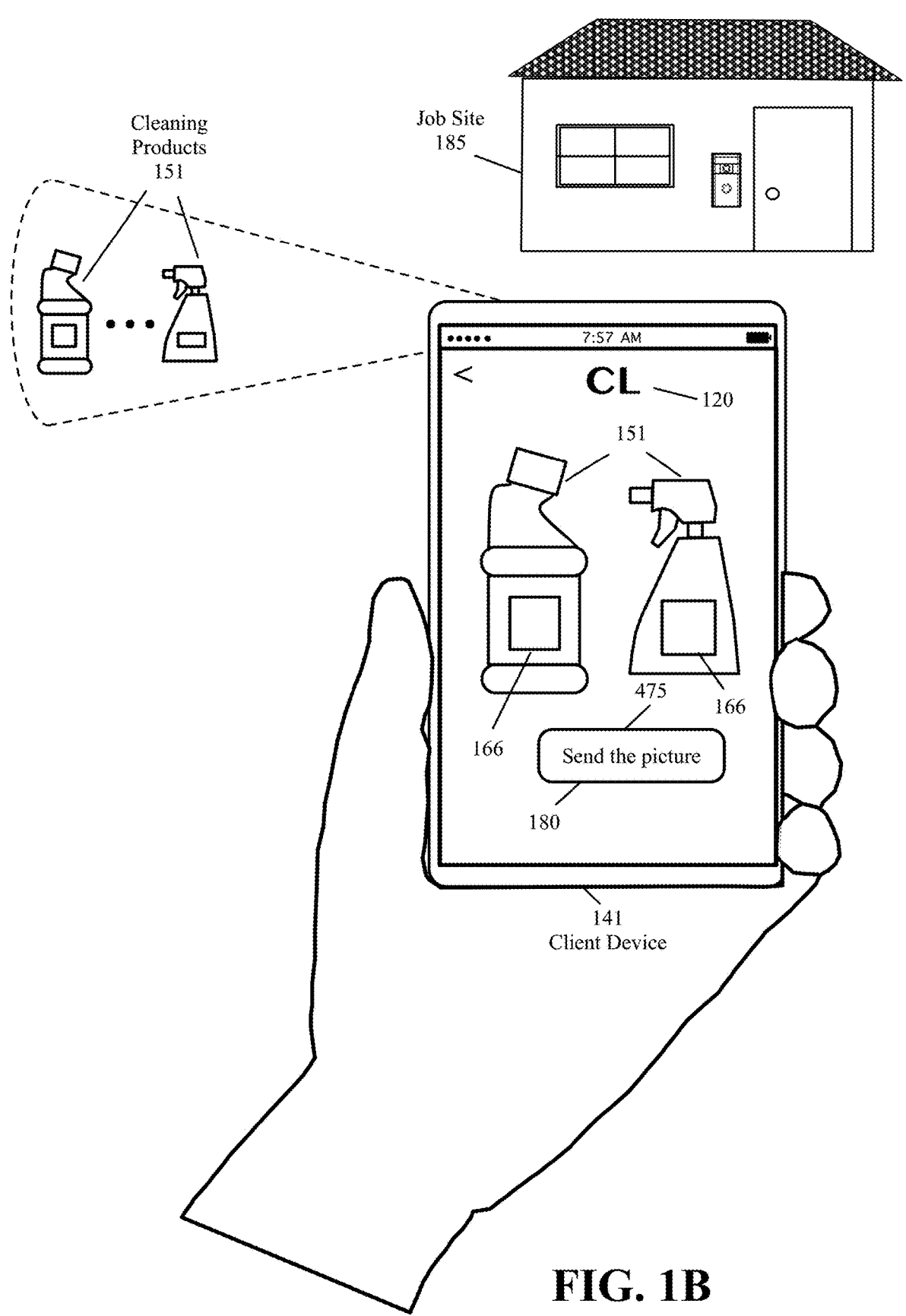
FIG. 1B is a functional diagram illustrating the client device of a cleaning worker taking geotagged images of cleaning products within a threshold distance of a job site to provide the evidence for the chemicals and the products that are being carried to the job site, according to various aspects of the present disclosure.

FIG. 1B is a functional diagram illustrating the client device of a cleaning worker taking geotagged images of cleaning products within a threshold distance of a job site to provide the evidence for the chemicals and the products that are being carried to the job site, according to various aspects of the present disclosure. With reference to FIG. 1B, a threshold time prior to the start of the cleaning task, the janitorial service provider's servers 110 may instruct the client device 121 to turn on location sharing and enable geotagging of images taken by the camera. When the client device 141 reaches a threshold distance from the job site 185, the janitorial service provider's servers 110 may instruct the person associated with the client device 141 to turn on the camera and take pictures of the cleaning products that are carried to the job site 185.

The client device 141 may take one or more geotagged images (e.g., still images or video images) of the cleaning products 151. The image(s) may show the products 151 and/or the associated labels 166. The image(s) may be sent from the client device 141 to the janitorial service provider's servers 110 when the option 180 is selected. The janitorial service provider's servers 110 may analyze the images to determine the location of the images (e.g., whether the images were taken within a threshold distance of the job site), the name of the cleaning products 151, and/or the chemical ingredients of the cleaning products listed on the labels 166. The janitorial service provider's servers 110 may identify the chemical used in the cleaning products 151 from the chemicals listed on the labels and/or by searching the cleaning products' chemical ingredient database 172.

When the images are taken within a threshold distance from the job site, the cleaning products and their chemical ingredients are not among the cleaning products and chemicals that are to be avoided at the particular cleaning site, and the cleaning products and their chemical ingredients include the requested cleaning products and chemicals, the cleaning worker may receive clearance to go to the job site. Further details are provided below with reference to FIGS. 2A-2C.

Some embodiments may provide an application program (App) 120 (FIG. 1B) that may be used by the client devices 121-122 and 141-142. The application program may communicate with the janitorial service provider's servers 110 to exchange data. The janitorial service provider's servers 110 may communicate with the users of the client device 121-122 and 141-142 through the application program to send and receive instructions.

The client devices 121-122 may use the application program 120 to provide a description of the space and items that need cleaning, the time and date of the cleaning, and/or whether the request is for a one-time cleaning or for cleaning at a recurring schedule. The client devices 141-142 may use the application program to book available cleaning jobs and to communicate with the janitorial service provider's servers 110 and the client devices 121-122 during the cleaning jobs.

Figure 2A:
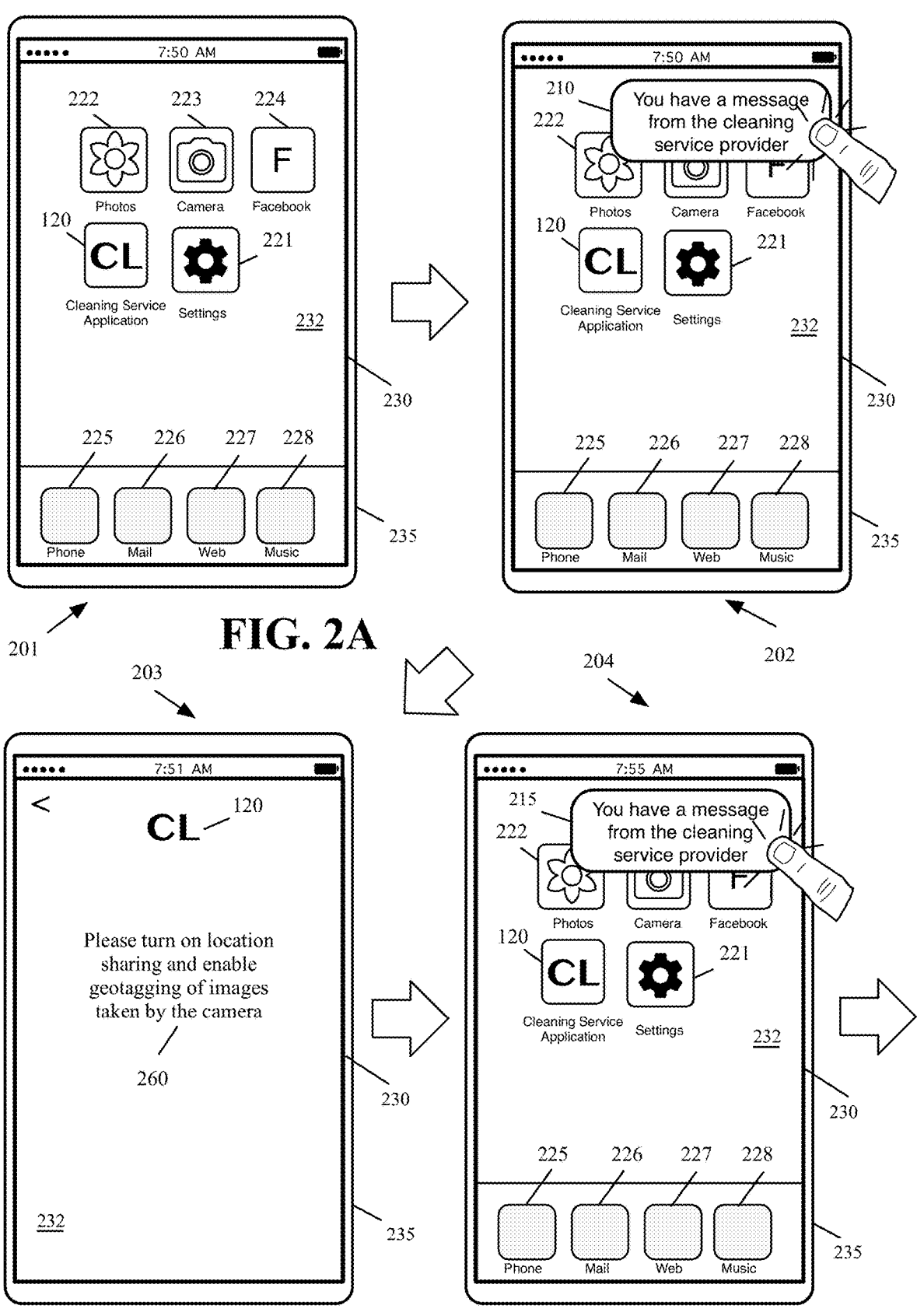
FIGS. 2A-2C are schematic front view of a client device that may include a cleaning service application program that ensures the correct cleaning products are brought to a cleaning site, according to various aspects of the present disclosure.
Figure 2B:
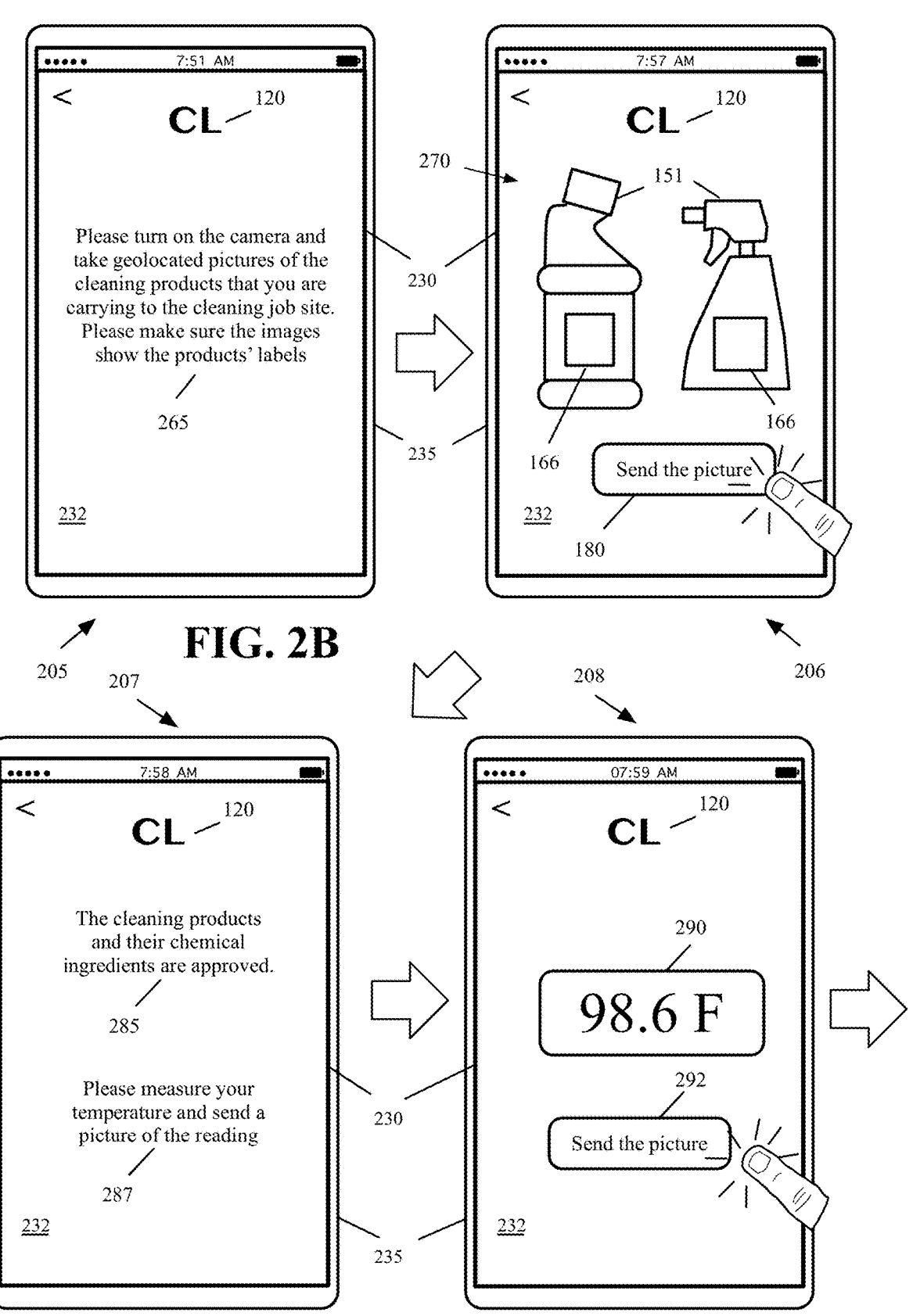
Figure 2C:
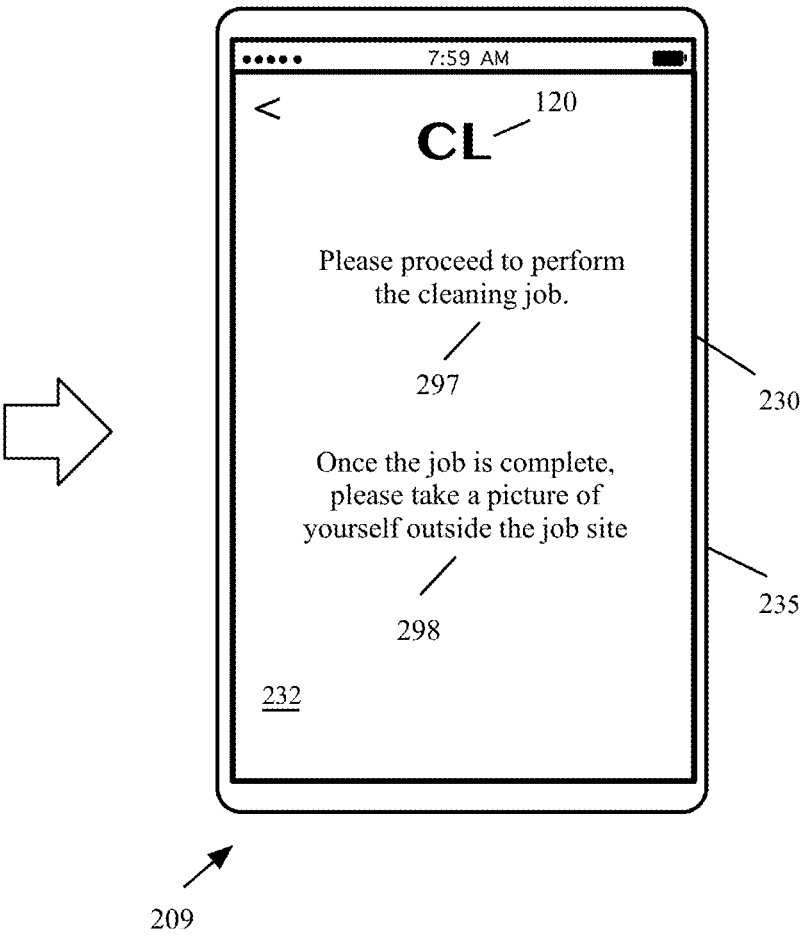

Some embodiments provide a system and method to ensure the cleaning products and chemicals that must be avoided during a cleaning job are not brough to the job site by the cleaning persons and/or the cleaning products that are specifically requested by a client are brought to the cleaning site. FIGS. 2A-2C are schematic front view of a client device 235 that may include a cleaning service application program 120 that ensures the correct cleaning products are brought to a cleaning site, according to various aspects of the present disclosure. The client device 235 may be any of the client devices 141-142 of FIG. 1A that are associated with cleaning persons.

FIGS. 2A-2C, as shown, include nine operational stages 201-209. Stage 201 shows a user interface (UI) 232 displayed on a display (e.g., a touchscreen) 230 of the client device 235, which may include several selectable UI items (e.g., icons) of several applications 120 and 221-228.

In the example of FIGS. 2A-2C, the person associated with the client device 235 has an upcoming booking and is heading to the cleaning job site. In stage 202, a banner 210 may be displayed (e.g., as a pop-up message) on the UI 232 of the client device 235 indicating that a message from the cleaning service provider is received. The janitorial service provider's servers 110 may compare the current time and date with the time and date of the booking associated with the person using the client device 235 and may send the message to the client device a threshold time (e.g., 2 hours, 1 hour, several minutes, etc.) prior to the start of the cleaning task.

As shown, the banner 210 is selected in stage 202. In response, the UI 232 in stage 203 may display the message 260 that is received from the cleaning service provider's servers 110 (FIG. 1). The message 260 may instruct the client device 235 to turn on location sharing and enable geotagging of images taken by the camera. In response, the person using the client device 235 may use an application, such as the settings application 221 to enable location tracking and geotagging of the images (e.g., if those features have not been previously enabled).

In stage 204, a banner 215 may be displayed (e.g., as a pop-up message) on the UI 232 of the client device 235 indicating that a message from the cleaning server provider is received. The janitorial service provider's servers 110 may compare the current location of the client device 235 with the location of the job site and may send the message to the client device 235 when the client device 235 is within a threshold distance of the cleaning job site.

Figure 3:
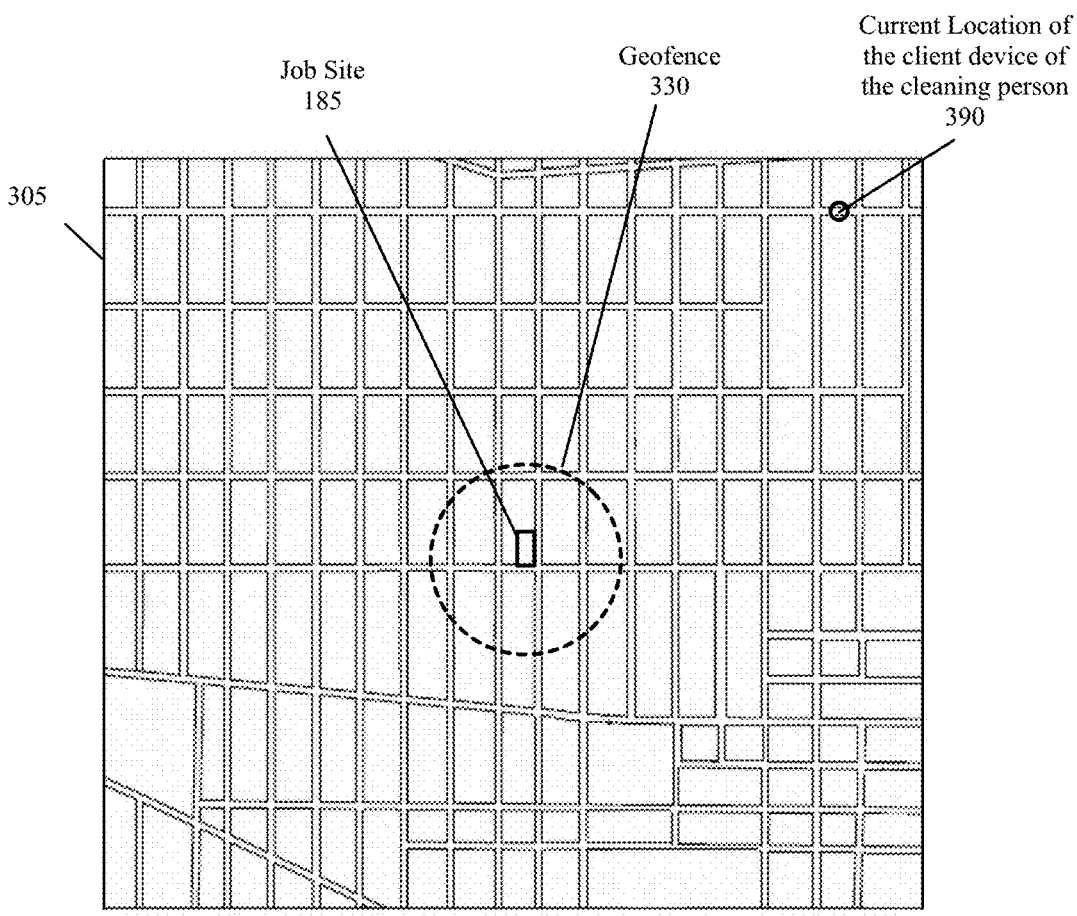
FIG. 3 is a schematic front view of an electronic device that may include an application program that provides a user interface for identifying the location of a client device associated with a cleaning person, according to various aspects of the present disclosure.

FIG. 3 is a schematic front view of an electronic device that may include an application program that provides a user interface for identifying the location of a client device associated with a cleaning person, according to various aspects of the present disclosure. With reference to FIG. 3, the user interface 305 may be displayed on the display of an electronic device such as a janitorial service provider's server 110 of FIG. 1A. The user interface 305 may be provided, for example, and without limitations, by an application program that may be installed on the server and/or after selecting a browser link to a website that may provide the location updates.

As shown, a geofence 330 may be defined around the job site 185. The geofence 330 may define a region around the job site 185 to determine whether the client device 235 has reached within a threshold distance of the job site 185 is in order to send the message 265 of FIG. 2B to the client device 235. The geofence 330 may be defined as a region (e.g., a circle, a rectangle, an arbitrary shape, etc.) within the threshold distance around a point in the job site 185. The geofence 330 may define the region that a cleaning work may turn on the camera of their client device and take pictures of the cleaning products that are being carried to the job site 185. The UI 305 may also display the current location 390 of the client device of the cleaning person.

Referring back to FIG. 2A, the banner 215 may be selected in stage 204. In response, the UI 232 may display the message 265 that is received from the cleaning service provider's servers in stage 205. The message 265 may instruct the client device 235 to turn on the camera and take geolocated pictures of the cleaning products that the person associated with the client device 235 is carrying to the job site. The message 265 may instruct to make sure the images show the product's label.

In response, one or more geotagged images (e.g., still images or video images) 270 may be taken by the camera of the client device 235. For example, one or more geotagged images may be taken as described above with reference to FIG. 1B. The image(s) may show the products 151 and/or the associated labels 166. The image(s) 270 may be sent to the janitorial service provider's servers 110 (FIG. 1A) when the option 180 is selected. It should be noted that images may be sent to the service provider's servers one at a time (as shown) or several images may be selected (e.g., from a recently taken album) and sent together to the janitorial service provider's servers.

The janitorial service provider's servers (FIG. 1A) may analyze the images to determine the location of the images (e.g., whether the images were taken within a threshold distance of the job site), the name of the cleaning products 151, and/or the chemical ingredients of the cleaning products 151. The janitorial service provider's servers may determine the chemical ingredients of the cleaning products 151 from the images of the labels 166 and/or by searching the cleaning products' chemical ingredient database 172.

When the images are taken within a threshold distance from the job site, the cleaning products 151 and their chemical ingredients are not among the cleaning products and chemicals that are to be avoided at the particular cleaning site, and the cleaning products 151 and their chemical ingredients include the requested cleaning products and chemicals, a message 285 may be received at stage 207 indicating that the products and their chemical ingredients are approved.

Some embodiments may optionally display a message 287 in stage 207 requesting the person associated with the client device 235 to take their body temperature and send a picture of the reading. As shown in stage 208, the image 290 of the temperature reading may be taken and may be sent to the janitorial service provider's servers by selecting the option 292.

In stage 209, a message 297 may be received from the janitorial service provider's servers indicating that the cleaning person may proceed to perform the cleaning job. A message 298 may be received from the janitorial service provider's servers requesting the cleaning person to take a picture of themselves once the cleaning job is complete and they are outside the job site.

The present embodiments, as described with reference to FIGS. 1A-1B and 2A-2C, provide the technical advantage of using geolocation tracking, receiving and analyzing the geolocated images of cleaning products and chemical that are carried to a cleaning job site to ensure a cleaning worker that is within a threshold distance of a job site is not carrying the cleaning products and chemical that has to be avoided at the cleaning site, to ensure that the cleaning worker is carrying the requested cleaning products and chemicals, and to ensure that the cleaning worker is healthy before entering a job site.

The janitorial service provider's servers 110 may receive requests from the client devices 121-122 for cleaning workers (e.g., one or more persons) to be sent to a job site, such as, a home, a private office, a government office, etc., to perform cleaning. FIGS. 4A-4D are schematic front view of a client device 435 that may include a cleaning service application program that may interact with a cleaning customer, according to various aspects of the present disclosure. The figure illustrates, through thirteen stages 401-413, a client device 435 using an application program 120 to provide information regarding a cleaning task.

With reference to FIGS. 4A-4D, stage 401 may display similar information as stage 201 of FIG. 2A. As shown in stage 401, the cleaning service application 120 is selected in stage 401. In response to the selection of the cleaning service application 120, the UI 232 in stage 402 may display one or more introductory messages 491 and several options 437-438.

Figure 4A:
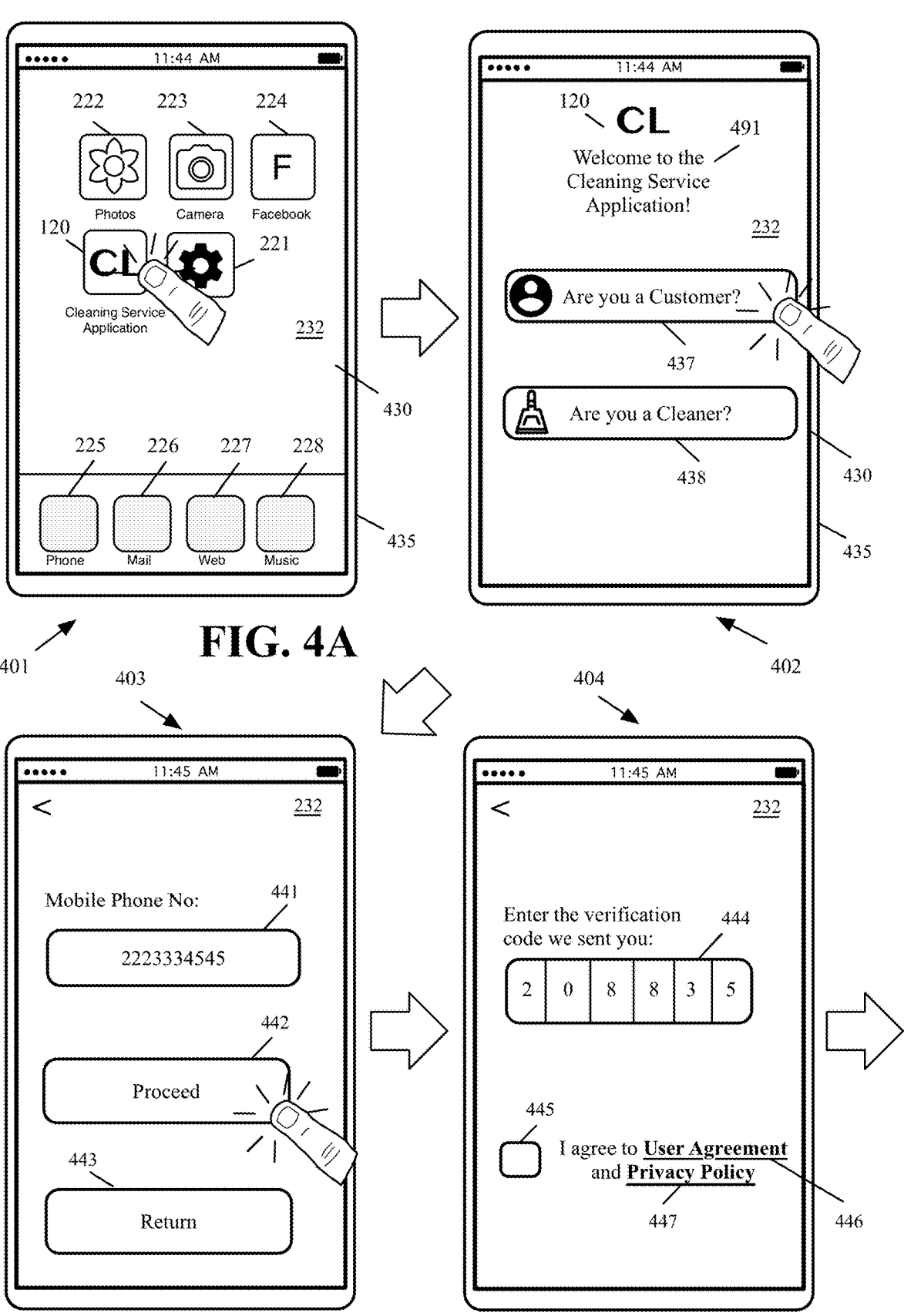
FIGS. 4A-4D are schematic front view of a client device that may include a cleaning service application program to interact with a cleaning customer, according to various aspects of the present disclosure.
Figure 4B:
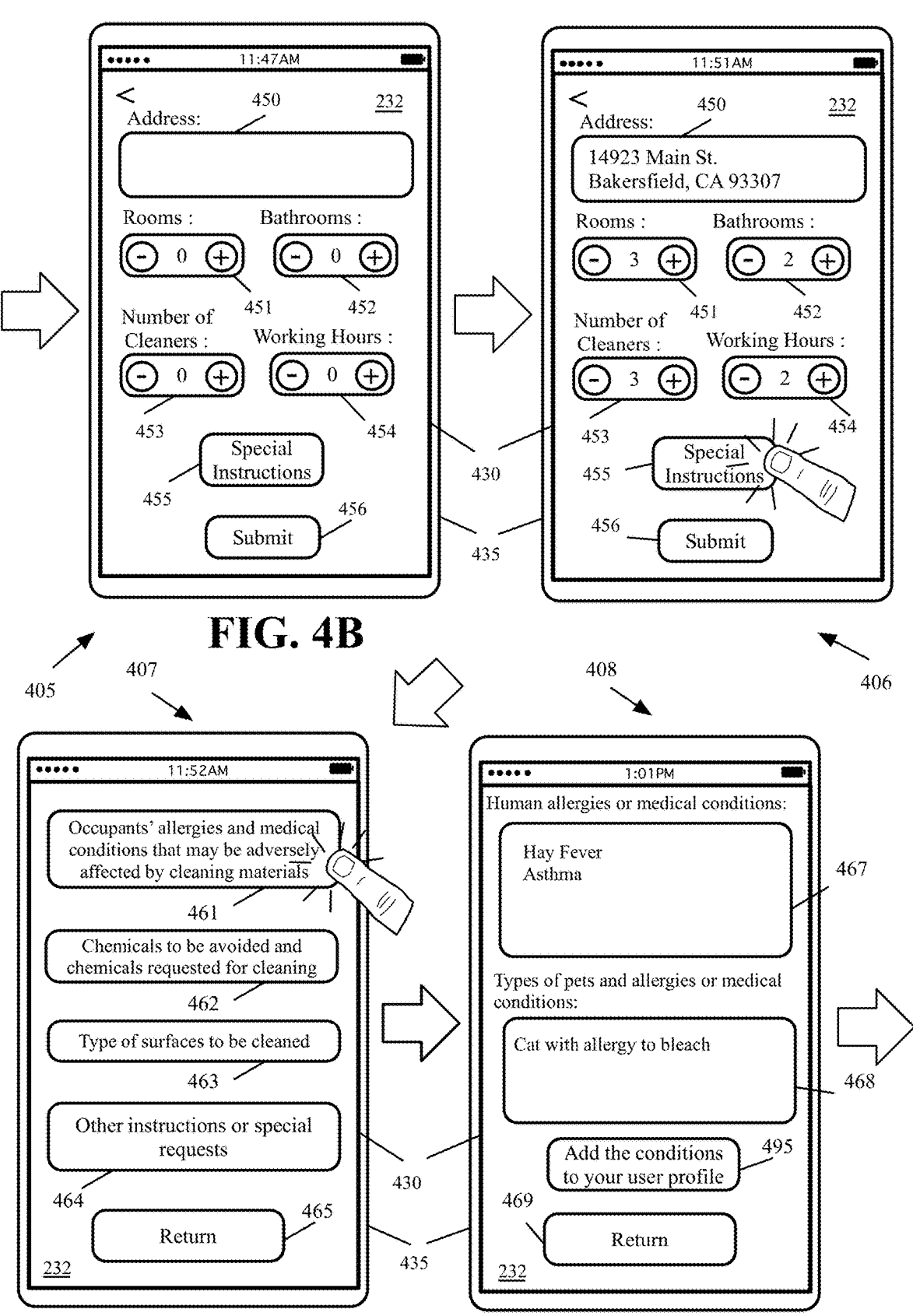
Figure 4C:
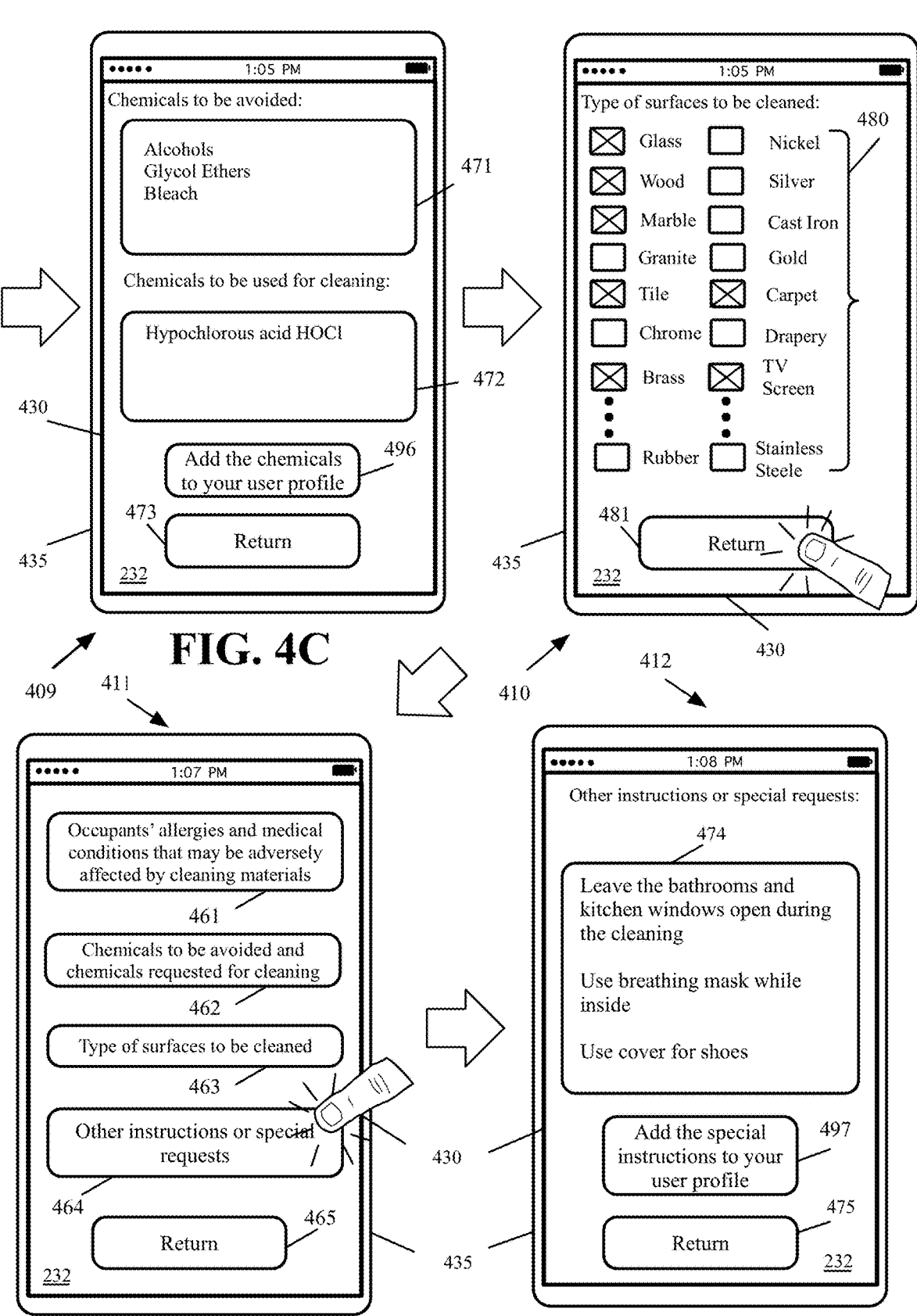

The application program 120, in some embodiments, may provide different UI options for the persons that require cleaning services and the persons that provide cleaning services. In the example of FIG. 4A, the option 437 is selected in stage 402 indicating the person associated with the client device 435 may require cleaning services. For example, the client device 435 may be one of the client devices 121-122 of FIG. 1A.

In response to selecting the option 437, the UI 232 may provide a display area 441 for entering an identification, such as, a phone number or an email (in the depicted example a phone number is requested), an option 442 to proceed, and an option 443 to return to the previous page. It should be noted that other embodiments may require other types of identifications, such as, for example and without limitations, a username and a password.

In response to selecting the option 442, the application program may send a verification code to the mobile phone number provided in stage 403. As shown in stage 404, the verification code may be entered in the display area 444. The person using the mobile device 435 may select the option 445 agreeing to the user agreement and the privacy policy, both of which may be available by selecting the associated links 446 and 447, respectively.

In stage 405, the UI 232 may provide a display area 450 for entering the property address that requires cleaning (the job site), a tool 451 for identifying the number of rooms, a tool 452 for identifying the number of bathrooms, a tool 453 for identifying the number of cleaners required, a tool 454 for identifying the number of hours requested, an option 455 for entering special instructions, and an option 456 for submitting the cleaning request.

In stage 406, the requested information is provided and the option 455 is selected to provide special instructions. In response to selecting the option 455, the UI 232 may display several options 461-465 in stage 407. The option 461 may be selected to specify the occupants' allergies and medical conditions that may be adversely affected by cleaning products and their chemical ingredients. The option 462 may be selected to identify the chemicals to be avoided and the chemicals that are requested for cleaning. The option 463 may be selected to specify the type of surfaces to be cleaned. The option 464 may be selected to enter other instructions or special requests (e.g., a request to leave the kitchen windows open during the cleaning or not letting a pet out of the building). The option 465 may be selected to return to the previous page.

Stage 408 displays the UI 232 after the option 461 is selected in stage 407. In stage 408, the UI 232 may provide a display area 467 for entering human related allergies or medical conditions, a display area 468 for entering the types of pets and their allergies or medical conditions, an option 495 to add the entered conditions to the user's profile, and an option 469 to return to the pervious page. As shown, the human allergies or medical conditions and/or the types of pets and their allergies and medical conditions may be specified in stage 408. As described below, the present embodiments enforce strict privacy measurements to ensure private information of the users are kept confidential. For example, the private information of the users may be kept their profiles and may not be shared with other users or administrators of system 100.

Stage 409 displays the UI 232 after the option 462 is selected in stage 407. In stage 409, the UI 232 may provide a display area 471 for specifying the chemicals to be avoided, a display area 472 for specifying the chemicals that are requested, an option 496 to add the chemicals to be avoided and the chemicals to be used for cleaning to the user's profile, and an option 473 to return to the pervious page. As shown, the chemicals to be avoided and the chemicals to be used may be specified in stage 409.

Stage 410 displays the UI 232 after the option 463 is selected in stage 407 (stage 407 is not shown immediately prior to stage 410 for brevity). In stage 410, the UI 232 may provide several options 480 for specifying the type of surfaces that need to be cleaned and an option 481 to return to the pervious page. As shown, the type of surfaces that need to be cleaned may be specified in stage 410. The option 481 may be selected in stage 410 to return to the previous page.

In response, the UI 232 in stage 411 may display the same information of as stage 407. The option 464 may be selected in stage 411. In response, the UI 232 in stage 412 may provide a display area 474 for specifying any other instructions or special requests that the user may have. As shown, several additional instructions and special requests are specified in the example of stage 412. The UI 232 in stage 411 may provide an option 497 to add the additional instructions and special requests to the user's profile, and an option 475 to return to the pervious page.

When the option 465 is selected in stage 411, the UI 232 in stage 413 may display the same information of as stage 406. When the option 456 is selected in stage 413, the application program may send the requested cleaning task to the janitorial service provider's servers 110 of FIG. 1A.

Some embodiments create profiles for users and provide the users with the tool to include their preference in their profiles. For example, as discussed above with reference to option 495 provided in stage 408, option 496 provided in stage 409, and the option 497 provided in stage 412, the UI 232 of the present embodiments provides the technical advantage of allowing a user to add detailed cleaning preferences, sensitivities, health and environmental concerns to tailor product recommendations and cleaning system optimizations.

The janitorial service provider's servers 110 may store the cleaning job description (e.g., the types of surfaces to be cleaned, the products or chemicals to be avoided, the requested cleaning products and chemicals, and/or the other instructions or special requests associated with the cleaning request) in a storage, such as the cleaning job description database 174. When the client device that has sent the request is associated with a new client, the client information may be stored in the cleaning customers database 176. The client's private data, such as, the occupants' allergies and medical conditions, may be kept as confidential data in the user's profile. The service provider's servers 110 may use the occupants' allergies and medical conditions to identify the products and chemicals to avoid and the products and chemicals that are safe for a cleaning job but may not share the clients' private date with humans or third-party entities.

With continued reference to FIG. 1A, the janitorial service provider's servers 110 may receive cleaning requests from the client devices 121-122 (e.g., as described above with references to FIGS. 4A-4D). The janitorial service provider's servers 110 may provide the cleaning request to the client devices 141-142 of the cleaning persons to find the cleaning worker(s) required for the requested cleaning tasks. The janitorial service provider's servers 110 may provide the cleaning request by sending push notifications (e.g., text messages or emails), by providing a website that may be accessible to the client device 121-122 and 141-142, or by an application program.

Figure 5:
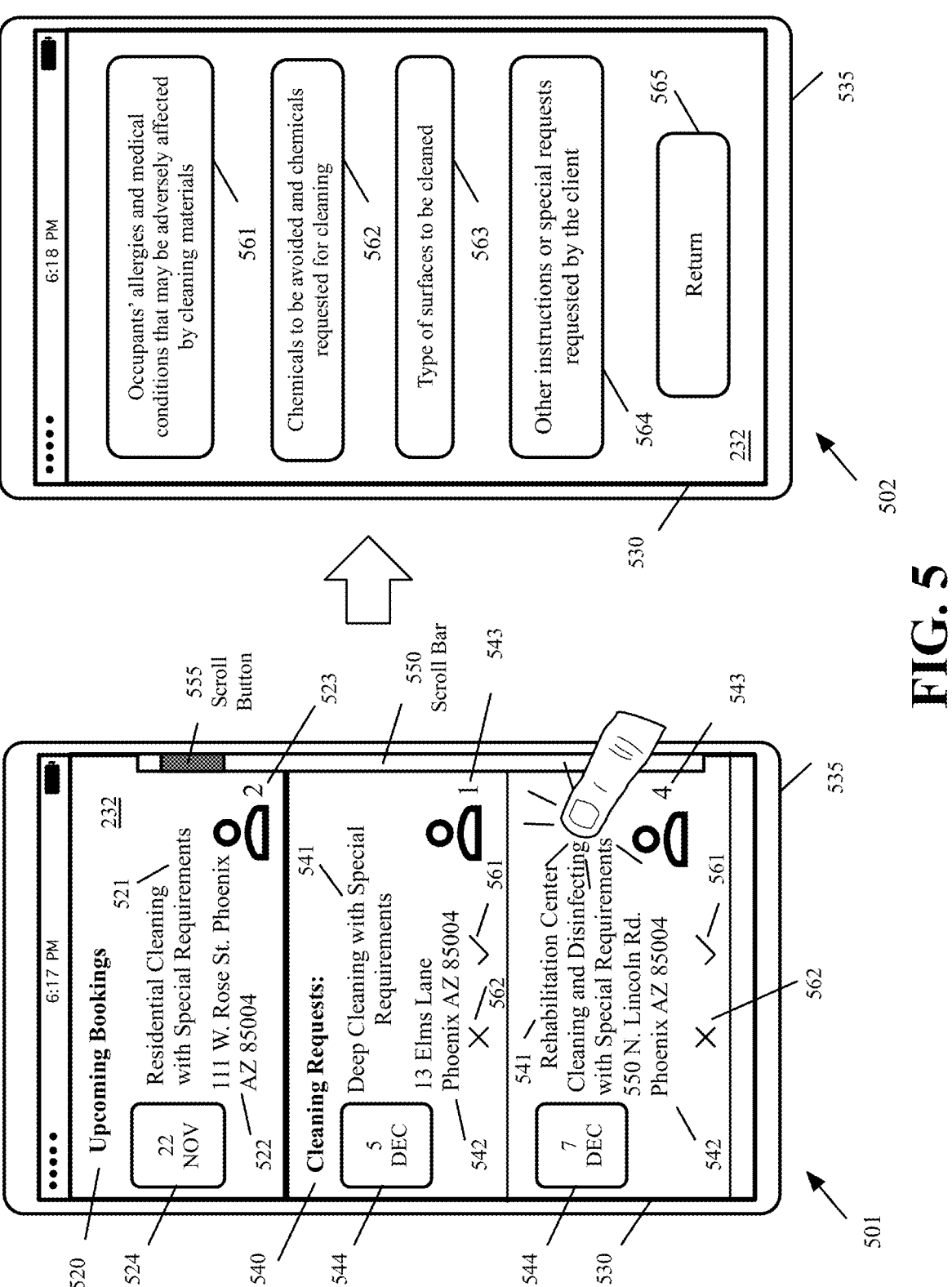
FIG. 5 is a schematic front view of a client device that may include a cleaning service application program to interact with a cleaning worker, according to various aspects of the present disclosure.

The application program 120, in some embodiments, may include a UI for the cleaning workers to review and accept their upcoming tasks and the available cleaning tasks. FIG. 5 is a schematic front view of a client device 535 that may include a cleaning service application program that may interact with a cleaning service worker, according to various aspects of the present disclosure. The figure illustrates a UI 232 that may be displayed on a display (e.g., a touchscreen) 530 of the client device 535. The client device 535 may be, for example, any of the client devices 141-142 of FIG. 1A.

The figure, as shown, includes two operational stages 501-502. The UI 232 in stage 501 may be displayed after the option 438 is selected in stage 402 of FIG. 4A and similar information as described with reference to stages 403-404 of FIG. 4A are received by the client device 535.

As shown in stage 501, the UI 232 may display one or more upcoming bookings 520 and/or one or more cleaning requests 540. The upcoming bookings 520 are the tasks that are already accepted by, and assigned to, the user of the client device 553. For each upcoming booking 520, the UI 232 may display a brief information, such as, the date 524 of the cleaning job, the type of cleaning 521, the address of the property to perform the cleaning 522, and the number of persons 523 required for performing the cleaning. Further details of each booking may be displayed when the booking is selected on the UI 232.

For each cleaning request 540, the UI 232 may display brief information, such as, the date 544 of the task, the type of cleaning required 541, the address of the property to perform the task 542, and the number of persons 543 required for performing the task. Further details of each task may be displayed when a task is selected on the UI 232. The UI 232 may also provide a scroll bar 550 and a scroll button 555 to display additional upcoming bookings 520 and/or cleaning requests 540.

In stage 501, one of the cleaning requests is selected. In response, the UI 232 in stage 502 may display several options 561-564 to display further information about the cleaning task. Selecting any of the 561-564 may display information that was entered for the cleaning task, for example, as described above with reference to options 461-464 of FIG. 4B. The UI 232 may provide an option 565 to return to the previous page.

The UI 232 in stage 501 may provide an option 561 to accept each cleaning request and an option 562 to discard a cleaning request. It should be noted that discarding a cleaning request only removes the cleaning request from the UI displayed on the display 530 of the client device 535. The cleaning request may be displayed on the UI of any other client device that has not discarded that cleaning request.

Any cleaning request that is selected, may be added to the bookings of the client device 535 and may not be displayed as a cleaning request to any other client devices. When the client device 535 is associated with a new cleaning worker (e.g., when the client device is assigned to a worker by an employer), the cleaning worker's identification, address, work experience, etc., may be received through the UI 232 and may be sent to the janitorial service provider's servers 110.

Figure 6B:
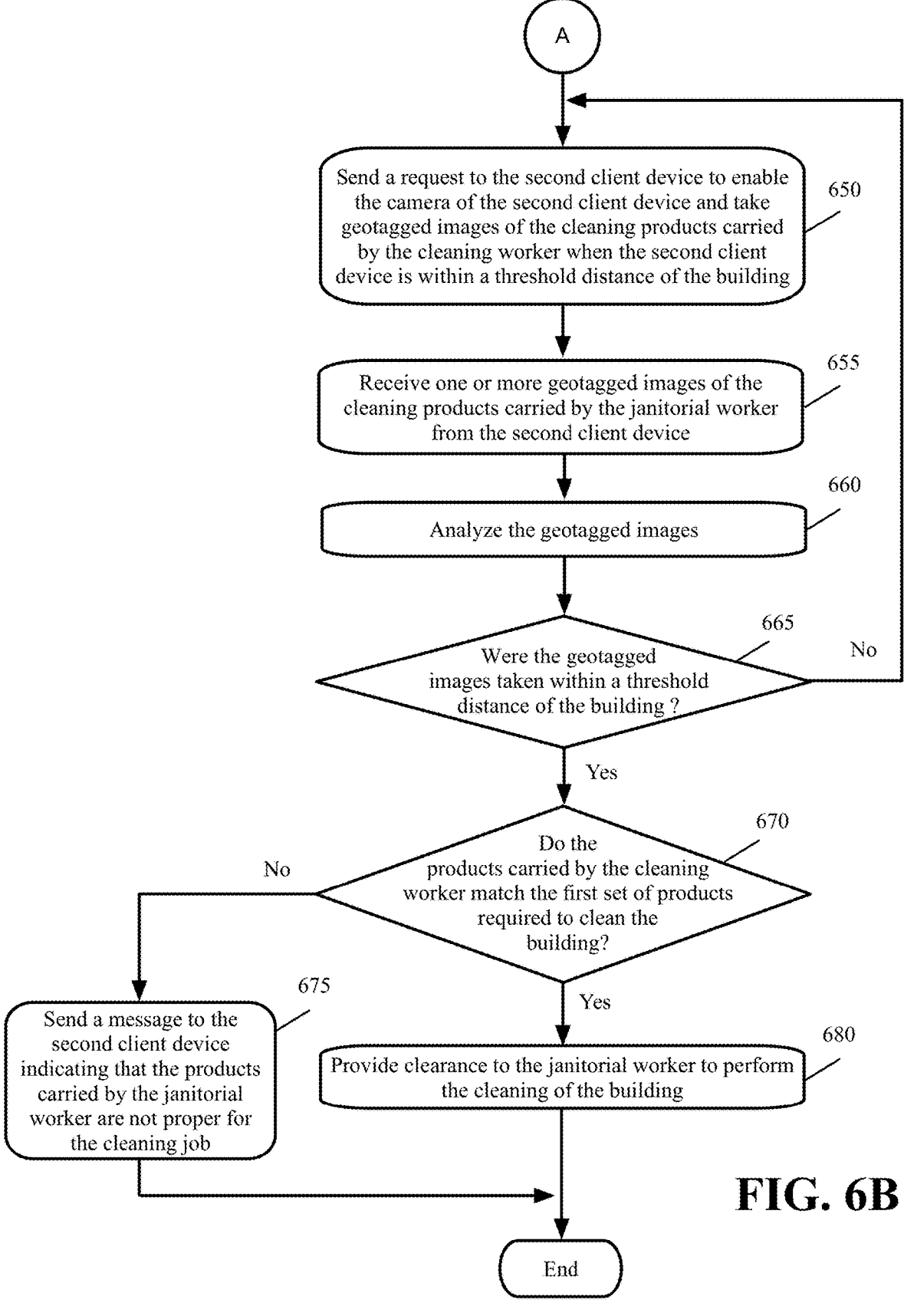

FIGS. 6A-6B are a flowchart illustrating an example process 600 for ensuring that cleaning products and their chemical components are safe for a particular cleaning job, according to various aspects of the present disclosure. The process 600, in some of the present embodiments, may be performed by the processor of an electronic device, such as a janitorial service provider server 110 of FIG. 1A.

Figure 4D:
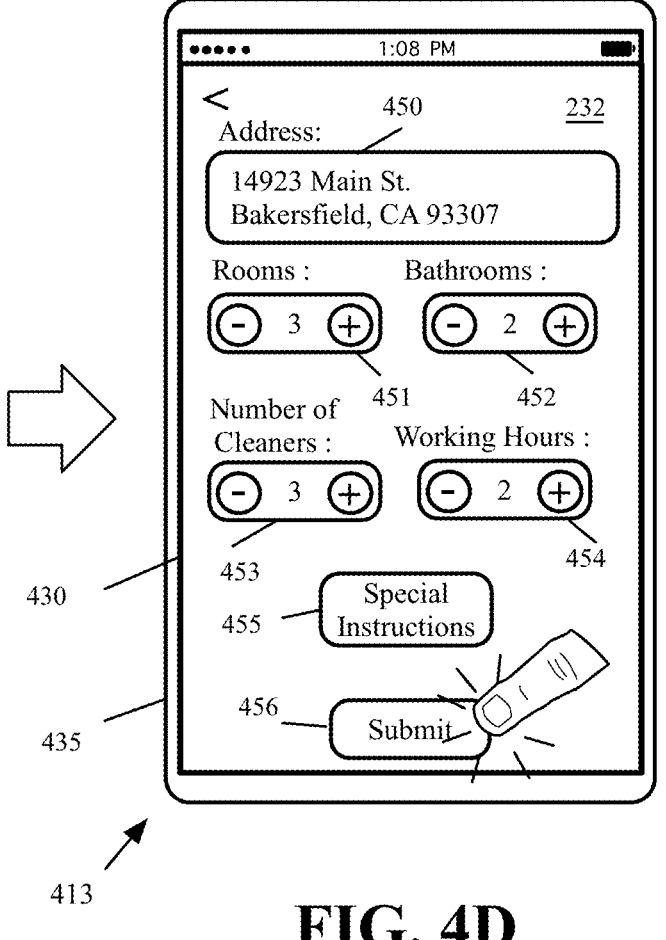

With reference to FIGS. 6A-6B, a request may be received (at block 605) from a first client device for cleaning a building, the request may include time and date of cleaning, one or more health issues of occupants of the building, and the identification of items that require cleaning. For example, a janitorial service provider's server 110 of FIG. 1A may receive the request when the option 456 in stage 413 of FIG. 4D is selected.

Next, one or more cleaning products may be identified (at block 610) for cleaning the items that require cleaning. For example, the cleaning request may have identified one or more types of surfaces to be cleaned as described above with reference to stage 410 of FIG. 4C. The processor of the janitorial service provider's server 110 of FIG. 1A may use the type of surfaces to be cleaned and may identify a plurality of cleaning products that are safe for cleaning the surface from a database, such as, the safe products for cleaning specific items database 173.

For example, if the items that require cleaning include marble the janitorial service provider's server 110 may exclude products that contain vinegar or lemon to avoid damaging the marble. As another example, if the items that require cleaning include granite, the janitorial service provider's server 110 may exclude products that contain bleach, vinegar, lemon, and hydrogen peroxide to avoid damaging the granite.

Next, the chemical ingredients of the cleaning products may be identified (at block 615). For example, the processor of the janitorial service provider's server 110 may use a database, such as the cleaning products' ingredient database 172 of FIG. 1A. A first set of one or more cleaning products that are safe for cleaning of the building may be identified (at block 625) based on the allergies and medical conditions of the occupants of the building and the ingredients of the cleaning products.

For example, the processor of the janitorial service provider's server 110 may use the information associated with the cleaning request, such as, for example, and without limitations, the types of surfaces to be cleaned, the occupants' allergies and medical conditions, the products or chemicals to be avoided, the requested cleaning products and chemicals, and/or the other instructions or special requests associated with the cleaning request to identify the set of cleaning products that are safe for cleaning the building. The processor of the janitorial service provider's server 110 may use information from a database, such as the safe products for health issues database 175 of FIG. 1A to identify cleaning products that are safe for the allergies and medical conditions of the occupants of the building. The processor of the janitorial service provider's server 110 may use measurements that are taken by microbial detection sensors 161 at a job site to select safe products and chemicals as well cleaning methods that are required for a specific job site.

The processor of the janitorial service provider's server 110 may determine that an occupant of the building has skin allergy and may eliminate any products that contains formaldehyde. As another example, the processor of the janitorial service provider's servers 110 may determine that an occupant of the building has asthma; and eliminating any products that contains phthalates or Quaternary ammonia compounds (QUATS). As another example, the processor of the janitorial service provider's servers 110 may determine that an occupant of the building has respiratory system irritation condition, skin irritation condition, and/or an eye irritation condition and may eliminate any products that contains methylisothiazolinone or ammonium hydroxide.

The time and date, the identification of the building, the identification of the first set of one or more cleaning products, and/or the number of cleaning workers needed for the cleaning task may be provided (at block 630) to the electronic devices of several cleaning workers. For example, the processor of the janitorial service provider's server 110 may provide the information regarding the cleaning task to the client devices of a plurality of cleaning workers as described above with reference to FIGS. 1A and 5.

A booking may be received (at block 635) from a second client device associated with a cleaning worker to clean the building using the first set of cleaning products at the requested time and date. For example, the processor of the janitorial service provider's server 110 may receive a booking for the cleaning task when the option 561 associated with one of the cleaning requests 540 is selected in stage 501 of FIG. 5.

A request may be sent (at block 640) to the second client device a threshold time before the time and date of the cleaning task to turn on location sharing, and geotagging of the images taken by the camera of the second client device. For example, the processor of the janitorial service provider's server 110 may send the message 260 to the client device 235 of the cleaning worker, as described above with reference to stage 203 of FIG. 2A.

A request may be sent (at block 650) to the second client device to enable the camera of the second client device and take geotagged images of the set of cleaning products carried by the cleaning worker when the second client device is within a threshold distance of the building. For example, the processor of the janitorial service provider's server 110 may send the message 265 to the client device 235, as described above with reference to stage 205 of FIG. 2B.

One or more geotagged images of the set of cleaning products carried by the janitorial worker may be received (at block 655) from the second client device. For example, the processor of the janitorial service provider's server 110 may receive one or more geotagged images of the set of cleaning products carried by the janitorial worker when the option 180 is selected in FIG. 1B or the option 180 is selected on the UI 232 of the client device 235 in stage 206 of FIG. 2B.

The geotagged images may be analyzed (at block 660). A determination may be made (at block 665) whether the geotagged images were taken within a threshold distance of the building. If not, the process 600 may proceed back to block 650, which was described above. Otherwise, a determination may be made (at block 670) whether the products carried by the cleaning worker match the first set of products required to clean the building. For example, the processor of the janitorial service provider's server 110 may identify the cleaning products and chemical that the cleaning worker is carrying by analyzing the geotagged images. The chemicals in the cleaning products may also be found by searching the cleaning products' chemical ingredient database 172. The processor of the janitorial service provider's server 110 may determine whether the cleaning products carried to the job site match the first set of products that are determined to be safe and/or required for the specific cleaning job.

If not, a message may be sent (at block 675) to the second client device indicating that the products carried by the janitorial worker are not proper for the cleaning job. The process 600 may then end. Otherwise, clearance may be provided (at block 680) to the janitorial worker to perform the cleaning of the building. For example, the processor of the janitorial service provider's server 110 may send the message 298 to the client device 235, as described above with reference to stage 209 of FIG. 2C. The process 600 may then end.

FIG. 7 is a functional diagram illustrating an example architecture of a client device, according to various aspects of the present disclosure. The client device 700 may be any of the client devices 121-122 and 141-142 of FIG. 1A. With reference to FIG. 7, the client device 700 may include one or more processors 705, computer readable media 710, input/output (I/O) interfaces 715, one or more communication interfaces 720, one or more cameras 725, an audio subsystem 730, a display 735, and other I/O devices 740.

The computer readable media 710 may include volatile memory (e.g., high-speed random access memory), non-volatile memory (e.g., flash memory), a combination of volatile and non-volatile memory, and/or any other type of memory. The computer readable media 710 may be non-transitory computer readable media. The computer readable media 710 may include different types of memory units, such as, read-only-memory, volatile read-and-write memory, and/or non-volatile read-and-write memory. The read-only-memory may store static data and instructions that are needed by the processor(s) 705. The non-volatile read-and-write memory may store instructions and data even when the power to the non-volatile memory is off. Some embodiments may use a mass-storage device (such as a magnetic or optical disk and its corresponding disk drive) as the non-volatile read-and-write memory.

The volatile read-and-write memory device may be random access memory and may be used as system memory. The system memory may store some of the instructions and data that the processor needs at runtime. In some embodiments, the processes of the present embodiments may be stored in the system memory, the non-volatile memory, and/or the read-only memory. From these various memory units, the processor(s) 705 may retrieve instructions to execute and data to process in order to execute the processes of some embodiments.

The communication interface(s) 720 may include interfaces to communicate wirelessly and/or through wire with one or more networks, such as the network(s) 190 of FIG. 1A. The communication interface(s) 720 may include wireless transceiver(s) such as, for example, and without limitations, cellular transceiver(s), WLAN transceiver(s), WiMAX transceiver(s), HD Radio transceiver(s), UWB transceiver(s), ZigBee transceiver(s), RFID transceiver(s), and/or 60 GHz transceiver(s). The client device 700 may include a global positioning system (GPS) receiver 780 to receive the location of the client device 700 from one or more satellites. The location may be used for geolocation determination (e.g., as described with reference to FIG. 5)

and/or for geotagging of the images taken by the camera(s) 725 (e.g., as described above with reference to FIGS. 1B and 2A-2D).

The camera(s) 725 may be coupled to one or more optical sensors 745 (e.g., a charged coupled device (CCD) optical sensor, a complementary metal-oxide-semiconductor (CMOS) optical sensor, etc.). The camera(s) 725 coupled with the optical sensors 745 may facilitate camera functions, such as image and/or video data capturing.

The audio subsystem 730 may be coupled to one or more speakers 750 to output audio. The audio subsystem 730 may be coupled to one or more microphones 755 to facilitate voice-enabled functions, such as voice recognition, digital voice recording, etc. The audio subsystem 730 may be used to receive user queries or instructions. The audio subsystem 730 may be used to provide instructions to the cleaning workers at a job site. The display 735, in some embodiments, may be a touchscreen. The other I/O devices 740 may include keyboard, cursor control devices (e.g., mouse, trackball, touchpad, etc.) and/or one or more buttons.

The I/O interfaces 715 may be coupled to various sensors and subsystems, including the wireless communication subsystem(s) 720, the camera(s) 725, the audio subsystem 730, the display 735, the other I/O devices 740, etc. The I/O interfaces 715 may enable communication between the processors 705 and different sensors and subsystems of the client device 700. Further details of client devices and other electronic devices of the present embodiments are described below with reference to FIG. 10.

FIG. 8 is a software block diagram 800 illustrating examples of software components of a janitorial service provider server, according to various aspects of the present disclosure. With reference to FIG. 8, the software components of a janitorial service provider server 110 (FIG. 1A) may include, but are not limited to, a product recommendation engine 810, a cleaning system optimizer 815, a user account and profile management module 820, a real-time environment analyzer 825, an inventory management module 830, and an educational and training resources module 835. The software components may be implemented in machine readable code and may be stored in memory units (e.g., the memory units 1020, 1030, and/or 1035 of FIG. 10. The software components may be executed by a processing unit (e.g., a process unit 1010 of FIG. 10).

The product recommendation engine 810 may analyze surface types, contaminant measurements, and user preferences to recommend the most effective and environmentally friendly cleaning products. The product recommendation engine 810 may perform data collection. The product recommendation engine 810 may collect information about different types of surfaces, such as hardwood floors, carpets, tiles, glass, etc. This may involve gathering data on the materials, textures, and finishes. The product recommendation engine 810 may gather data on common contaminants found on surfaces, such as dust, dirt, grease, stains, etc.

The product recommendation engine 810 may capture user preferences through surveys, user feedback, or previous purchase history. This may include preferences for specific brands, scents, eco-friendly options, etc. The product recommendation engine 810 may use the information the cleaning customers enter into their profiles (e.g., as described with reference to the options 495-497 of FIGS. 4A-4D).

The product recommendation engine 810 may perform feature extraction by identifying key features for each surface type and contaminant. For example, certain cleaning agents might be more effective on specific contaminants or surfaces. The product recommendation engine 810 may be configured to take into account the identified features and use them to recommend cleaning products.

The product recommendation engine 810 may consider factors like environmental impact, user preferences, and the efficacy of products in removing specific contaminants from particular surfaces to make product recommendations. The product recommendation engine 810 may implement machine learning techniques, such as classification or recommendation algorithms, to learn patterns and relationships from the data.

The product recommendation engine 810 may utilize interaction with the user, for example, through user interfaces described above with reference to FIGS. 4A-4D, where users may input information about the surface type and contaminants they are dealing with. The users may specify preferences, such as eco-friendliness, scent preferences, or brand preferences. Based on the input provided by the user, the product recommendation engine 810 may generate recommendations for cleaning products. The recommendations may be ranked based on factors like effectiveness, environmental impact, and user preferences. The recommendations may promote the use of eco-friendly cleaning products and practices, contributing to sustainability efforts and reducing the environmental footprint.

The product recommendation engine 810 may implement machine learning and adaptation by implementing a feedback loop to collect user feedback after the completion of each cleaning job. The user interactions and feedback may be used to continuously improve the machine learning algorithm. The machine learning algorithm may learn over time based on the effectiveness of the product recommendation engine's recommendations and may adjust the suggestions accordingly.

The product recommendation engine 810 may receive ATP measurement data from hand held microbial detection sensors 161, thorough the client devices 141-142 of cleaning workers at the job site. The product recommendation engine 810 may use the ATP measurement data to select safe products for an ongoing cleaning job or for a future cleaning job at the site where the ATP measurements have been made.

The cleaning system optimizer 815 may utilize machine learning to understand the best cleaning methodologies for various surfaces, adapting to user habits, and recommending optimal cleaning systems for specific cleaning tasks based on the usage of the surface. Software components, such as the product recommendation engine 810 and the cleaning system optimizer 815 may implement one or more machine learning models for different tasks for a job site cleaning application. For example, one model may be focused on image recognition to identify different surfaces or cleaning products, while another model may be designed for natural language processing to understand user queries or instructions. The users may benefit from a tailored cleaning experience with optimal product recommendations and cleaning methodologies for different surfaces and conditions.

In the field, the machine learning model may communicate with the cleaning service application program 120, described above, to provide real-time recommendations or guidance to the cleaning workers. For example, the application 120 may receive suggestions for suitable cleaning products based on the type of surface or offer personalized cleaning schedules based on historical data.

The machine learning model may be improved over time by incorporating a feedback loop where user interactions and outcomes are used to continuously improve the model's performance. The feedback loop may include user ratings, feedback on suggested cleaning methods, or adjustments based on the user's preferences. The machine learning model may provide data filtering and privacy for the user-generated data. The machine learning model may be used to filter and process user-generated data. Privacy considerations are crucial, and strict measures are in place to ensure the responsible handling of user data. For example, the cleaning workers may not be able to see the reason (e.g., the cleaning client's health or safety issues) for the selection or avoidance of particular products chemicals at a job site.

The user account and profile management module 820 provides tools for the users to create profiles with detailed cleaning preferences, sensitivities, health and environmental concerns to tailor product recommendations and cleaning system optimizations (e.g., as described above with reference to FIGS. 4A-4D). The real-time environment analyzer 825 may utilize the weather information databases 178 and environmental information databases 179 to provide real-time suggestions for cleaning adjustments based on external conditions, ensuring optimal cleaning results. The real-time environment analyzer 825 may provide humidity-based recommendations. For example, if a weather database 178 (FIG. 1A) indicates high humidity levels, the real-time environment analyzer 825 may suggest using specific cleaning products that are effective in such conditions. High humidity may affect drying times, and using products optimized for these conditions may improve overall cleaning results.

The real-time environment analyzer 825 may receive ATP measurement data from hand held microbial detection sensors 161, thorough the client devices 141-142 of cleaning workers at the job site. The real-time environment analyzer 825 may provide feedback for the cleaning methods (e.g., deep cleaning) and/or the use of safe chemical that the cleaning workers may have brought to the job site based on the ATP measurement data.

The real-time environment analyzer 825 may consider the current temperature from the weather information databases 178 and may identify temperature-dependent cleaning products. For example, during colder weather, the real-time environment analyzer 825 may recommend using cleaning solutions that work well in lower temperatures, ensuring that the products remain effective and do not freeze. The real-time environment analyzer 825 may consider allergen alerts. For example, if an environmental information database 179 (FIG. 1A) reports high pollen or allergen levels, the cleaning application may provide suggestions for using air purifiers or adjusting cleaning practices to minimize allergen exposure. This may be especially useful for individuals with allergies or respiratory conditions.

The real-time environment analyzer 825 may consider the UV index and sunlight exposure. The knowledge of the UV index and sunlight intensity may inform the application 120 about optimal times for certain cleaning tasks. For example, real-time environment analyzer 825 may recommend cleaning tasks that involve sunlight exposure during times of the day when UV levels are lower to avoid potential health risks or product degradation. Such a feedback may be provided, for example, to a client who is scheduling a cleaning job using the UI of FIGS. 4A-4D.

The real-time environment analyzer 825 may provide outdoor cleaning timing recommendations. For example, the information about precipitation and upcoming weather events may be received from the weather information databases 178 and may be used to suggest optimal times for outdoor cleaning tasks. The real-time environment analyzer

825 may instruct the application program 120 to advise the users to postpone certain tasks if rain is expected shortly to avoid wasted effort.

The real-time environment analyzer 825 may provide suggestions based on environmental impact. Environmentally friendly practices may be promoted based on the weather conditions and precipitations received from the weather information databases 178. For example, on days with heavy rainfall, real-time environment analyzer 825 may suggest reducing the use of water-intensive cleaning methods since nature is providing a natural cleaning effect.

The real-time environment analyzer 825 may provide energy efficient recommendations. For example, if the environmental information database 179 indicate peak energy consumption times, the application may suggest scheduling energy-intensive cleaning tasks during off-peak hours to contribute to energy efficiency efforts. The real-time environment analyzer 825 may provide weather-resistant materials feedback to the users through the cleaning service application 120. For example, in regions with extreme weather conditions, the cleaning service application 120 may provide recommendations for using weather-resistant cleaning materials or methods to ensure longevity and effectiveness.

The inventory management module 830 assists users in managing their cleaning product inventory by tracking usage, expiration dates, and suggesting replenishments, minimizing waste, and ensuring the availability of necessary supplies. The educational and training resources module 835 may offer educational and training content on proper cleaning techniques, best practices, and the science behind different cleaning products, empowering users to make informed choices.

FIG. 9 is an example sequence diagram 900 illustrating message flows and operations performed for ensuring that safe cleaning products are selected and carried to a cleaning job site, according to various aspects of the present embodiments. With reference to FIG. 9, the first electronic device 901 may be a janitorial service provider's server 110 of FIG. 1A, the second electronic device 902 may be one of the client devices 121-122 of FIG. 1A, and the third electronic device 903 may be one of the client devices 141-142 of FIG. 1A.

As shown, a request for cleaning a building including time and date; health issues of the occupants; identification of items to be cleaned; and/or number of cleaning workers required may be received (at step 905) by the first electronic device 901 from the second electronic device 902. For example, the request may be received by the processor of the janitorial service provider's server 110 from the client device 435 as described above with reference to stages 405-413 of FIGS. 4B-4D and block 605 of FIG. 6A.

The first electronic device 901 may identify (at block 910) several cleaning products for cleaning the items to be cleaned. For example, the processor of the janitorial service provider's server 110 may identify several cleaning products for cleaning the items to be cleaned as described above with reference to block 610 of FIG. 6A.

The first electronic device 901 may identify (at block 915) the chemical ingredients of the plurality of cleaning products. For example, the processor of the janitorial service provider's server 110 may identify the chemical ingredients of the plurality of cleaning products as described above with reference to block 615 of FIG. 6A.

The first electronic device 901 may identify (at block 920) one or more products to use for cleaning based on the allergies and medical conditions of the occupants. For example, the processor of the janitorial service provider's server 110 may identify a first set of one or more cleaning products in the plurality of cleaning products that are safe for cleaning of the building based on the allergies and medical conditions of the occupants of the building and the ingredients of the plurality of cleaning products, as described above with reference to block 625 of FIG. 6A.

The first electronic device 901 may provide (at step 930) the time and date, the identification of the building, the identification of the set of one or more cleaning products, and the number of required cleaning workers to the third electronic device. For example, the processor of the janitorial service provider's server 110 may provide the information to an application program that is used by the client device 535 of a cleaning worker, as described above with reference to FIG. 5 and block 630 of FIG. 6A. In some embodiments, the processor of the janitorial service provider's server 110 may provide the information on a website that is accessible by the client devices of cleaning workers. In some embodiments, the processor of the janitorial service provider's server 110 may send push notifications to the client devices of the cleaning workers when a cleaning request is available that meeting one or more criteria set by the cleaning workers (e.g., the type of the cleaning job, time and date, location of the job site, number of required cleaning persons, etc.).

The first electronic device 901 may receive (at step 935) a booking from the third electronic device to clean the building with the set of products at the requested time and date. For example, the processor of the janitorial service provider's server 110 may receive a booking from the client device 535 (FIG. 5) of a cleaning worker when the option 561 associated with a cleaning request is selected.

The first electronic device 901 may send (at step 940) a request to the third electronic device to turn on location sharing and enable geotagging of images taken by the camera. For example, the processor of the janitorial service provider's server 110 may send a message, such as the message 260 described above with reference to stage 203 of FIG. 2A.

The first electronic device 901 may send (at step 945) a request to the third electronic device to turn on the camera and take geotagged images of the products being carried to the job site with the camera. For example, the processor of the janitorial service provider's server 110 may send a message, such as the message 265 described above with reference to stage 205 of FIG. 2A.

The first electronic device 901 may receive (at step 950) one or more geotagged images of the cleaning products carried to the job site. For example, the processor of the janitorial service provider's server 110 may receive one or more geotagged images of the cleaning products from the client device 235 of the cleaning worker when the option 280 is selected in stage 206 of FIG. 2B.

The first electronic device 901 may determine (at block 955) that the cleaning product images match products required for cleaning the building and the geotagged location indicates the images were taken within a threshold distance of the building. For example, the processor of the janitorial service provider's server 110 may determine that the geotagged images were taken within a threshold distance of the job site (as described above with reference to block 665 of FIG. 6B) and the cleaning products carried by the cleaning worker match the set of products required to clean building (as described above with reference to block 670 of FIG. 6B).

The first electronic device 901 may send (at step 960) a clearance to the third electronic device to proceed to perform the cleaning job. For example, the processor of the janitorial service provider's server 110 may send the message 298 to the client device 235 of the cleaning worker, as described above with reference to stage 209 of FIG. 2C.

Some of the above-described features and applications are implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which may be read into memory for processing by a processor. Also, in some embodiments, multiple software inventions may be implemented as sub-parts of a larger program while remaining distinct software inventions. In some embodiments, multiple software inventions may also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

FIG. 10 conceptually illustrates an electronic system 1000 with which some embodiments of the invention (e.g., the servers 110, the client devices 121-122 and 141-142, etc., described above) are implemented. The electronic system 1000 may be used to execute any of the control, virtualization, or operating system applications described above. The electronic system 1000 may be a computer (e.g., desktop computer, personal computer, tablet computer, server computer, mainframe, blade computer etc.), a smartphone, a personal digital assistant (PDA), or other types of electronic device. Such an electronic system includes various types of computer readable media and interfaces for various other types of computer readable media. The electronic system 1000 may include a bus 1005, processing unit(s) 1010, a system memory 1020, a read-only memory (ROM) 1030, a permanent storage device 1035, input devices 1040, and output devices 1045.

The bus 1005 collectively represents all system, peripheral, and chipset buses that communicatively connect the numerous internal devices of the electronic system 1000. For instance, the bus 1005 communicatively connects the processing unit(s) 1010 with the read-only memory 1030, the system memory 1020, and the permanent storage device 1035.

From these various memory units, the processing unit(s) 1010 retrieve(s) instructions to execute and data to process in order to execute the processes of the invention. The processing unit(s) may be a single processor or a multi-core processor in different embodiments.

The read-only-memory 1030 stores static data and instructions that are needed by the processing unit(s) 1010 and other modules of the electronic system. The permanent storage device 1035, on the other hand, is a read-and-write memory device. This device is a non-volatile memory unit that stores instructions and data even when the electronic system 1000 is off. Some embodiments of the invention use a mass-storage device (such as a magnetic or optical disk and its corresponding disk drive) as the permanent storage device 1035.

Other embodiments use a removable storage device (such as a flash drive, memory cards, etc.) as the permanent storage device. Like the permanent storage device 1035, the system memory 1020 is a read-and-write memory device. However, unlike storage device 1035, the system memory is a volatile read-and-write memory, such as random-access memory. The system memory stores some of the instructions and data that the processor needs at runtime. In some embodiments, the invention's processes are stored in the system memory 1020, the permanent storage device 1035, and/or the read-only memory 1030. From these various memory units, the processing unit(s) 1010 retrieve instructions to execute and data to process in order to execute the processes of some embodiments.

The bus 1005 also connects to the input and output devices 1040 and 1045. The input devices enable the user to communicate information and select commands to the electronic system. The input devices 1040 may include alphanumeric keyboards and pointing devices (also called "cursor control devices"). The input devices 1040, in some embodiments, may include cameras, sensors, microphones, near field communication (NFC) readers, and/or radio-frequency identification (RFID) readers. The input devices 1040, in some embodiments, may include pushbutton, switches, and/ or knobs. The output devices 1045 may include printers, speakers, light sources (e.g., flashlights), and display devices, such as cathode ray tubes (CRT), liquid-crystal displays (LCD), light-emitting diode (LED) displays. Some embodiments may include devices, such as a touchscreen, that function as both input and output devices. The output devices 1045, in some embodiments, may display images generated and/or received by the electronic system.

Finally, as shown in FIG. 10, bus 1005 also couples electronic system 1000 to a network 1025 through a network adapter (not shown). In this manner, the computer may be a part of a network of computers (such as a local area network ("LAN"), a wide area network ("WAN"), an Intranet, or a network of networks, such as the Internet. Any or all components of electronic system 1000 may be used in conjunction with the invention.

Some embodiments include electronic components, such as microprocessors, storage, and memory, that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some embodiments are performed by one or more integrated circuits, such as application specific integrated circuits (ASICs) or field programmable gate arrays (FPGAs). In some embodiments, such integrated circuits execute instructions that are stored on the circuit itself.

As used in this specification, the terms "computer", "server", "processor", and "memory" all refer to electronic or other technological devices. These terms exclude people or groups of people. For the purposes of the specification, the terms display or displaying means displaying on an electronic device. As used in this specification, the terms "computer readable medium," "computer readable media," and "machine readable medium" are entirely restricted to tangible, non-transitory, physical objects that store information in a form that is readable by a computer. These terms exclude any wireless signals, wired download signals, and any other ephemeral or transitory signals.

In a first aspect, an automated method of providing health security for cleaning a building is provided. The method may be performed by the processor of a janitorial service provider's server. The method receives a request from a first electronic device for cleaning a building. The request includes a time and a date of cleaning, a set of one or more health issues of occupants of the building, and the identification of items that require cleaning in the building. The method identifies several cleaning products for cleaning the items that require cleaning in the building. The method identifies chemical ingredients of the cleaning products. The method identifies a first set of one or more cleaning products from the several cleaning products for cleaning of the building based on the health issues of occupants of the building and the chemical ingredients of the cleaning products. The method provides the time and date, an identification of the building, and the identification of the first set of one or more cleaning products to electronic devices of several janitorial workers. The method receives a request from a second electronic device in the electronic devices of the janitorial workers to clean the building using the first set of cleaning products at the time and date of cleaning. A threshold time before the time and date of cleaning, the method sends a request to the second electronic device to turn on geolocation tracking, enable a camera of the second electronic device, and take geolocated images of a second set of cleaning products carried by the janitorial worker. The method receives, from the second electronic device, a set of one or more geolocated images of the second set of cleaning products. The method analyzes the set of one or more geolocated images. Based on the analysis, the method determines that the second electronic device is within a threshold distance of the building and the second set of cleaning products match the first set of products. The method provides a clearance to the janitorial worker to perform the cleaning of the building based on the determination.

In an embodiment of the first aspect, the method receives, by the server from the second electronic device, adenosine triphosphate (ATP) measurements made by a microbial detection sensor on a first surface in the building measurements. The method selects, by the processor of the server, at least one cleaning product in the first set of one or more cleaning products to clean the first surface based on the ATP measurements. The method sends, by the processor of the server, an instruction to the person associated with the second electronic device to use the at least one product on the first surface.

In another embodiment of the first aspect, the method receives, by the server from the second electronic device, ATP measurements made by a microbial detection sensor on a first surface in the building measurements. The method receives, by the server from the second electronic device, ATP measurements made by a microbial detection sensor on a first surface in the building measurements. The method selects, by the processor of the server, one or more cleaning products in the first set of one or more cleaning products to clean the first surface based on the ATP measurements. The method updates a profile of a user of the first client device to recommend the use of the one or more cleaning products for cleaning the first surface in furfure cleaning jobs of the building.

In another embodiment of the first aspect, the method receives cleaning product preferences from the first client device. the method updates a profile of a user of the first client device, by the processor of the server, based on the received product preferences, where identifying a first set of one or more cleaning products in the plurality of cleaning products for cleaning of the building further includes identifying a first set of one or more cleaning products based on the cleaning product preferences in the profile of the user of the first client device.

In another embodiment of the first aspect, identifying the first set of one or more cleaning products for cleaning of the building includes receiving, by the processor of the server, a range of temperature predictions at the time and date of cleaning from a weather information database and identifying the first set of one or more cleaning products from cleaning products that are recommended to work well in the predicted range of temperature at the time and date of cleaning.

In another embodiment of the first aspect, identifying the first set of one or more cleaning products for cleaning of the building includes receiving, by the processor of the server, precipitation predictions at the time and date of cleaning from a weather information database and identifying the first set of one or more cleaning products from cleaning products that are recommended to work well for the predicted precipitation at the time and date of cleaning.

In another embodiment of the first aspect, identifying the first set of one or more cleaning products for cleaning of the building further includes receiving, by the processor of the server, precipitation predictions at the time and date of cleaning from a weather information database and identifying the first set of one or more cleaning products from cleaning products that have less environmental impact in the predicted precipitation.

In another embodiment of the first aspect, identifying the first set of one or more cleaning products for cleaning of the building further include receiving, by the processor of the server, humidity predictions at the time and date of cleaning from a weather information database and identifying the first set of one or more cleaning products from cleaning products based on the humidity predications at the time and date of cleaning.

In another embodiment of the first aspect, the method further provides a plurality of time and date recommendations for cleaning of the building, by the server, based on information regarding precipitations and upcoming weather events in the region where the building located. The method receives the time and the date for cleaning of the building from the first electronic device based on the plurality of time and date recommendations.

In another embodiment of the first aspect, the method further provides a plurality of time and date recommendations for cleaning of the building, by the server, based on peak energy consumption times received from an environmental information database. The method receives the time and the date for cleaning of the building from the first electronic device based on the plurality of time and date recommendations.

In another embodiment of the first aspect, identifying the first set of cleaning products based on the health issues of occupants of the building and the ingredients of the plurality of cleaning products includes determining that an occupant of the building has asthma and eliminating any product in the plurality of products that contains phthalates.

In another embodiment of the first aspect, identifying the first set of cleaning products based on the health issues of occupants of the building and the ingredients of the plurality of cleaning products includes determining that an occupant of the building has asthma and eliminating any product in the plurality of products that contain QUATS.

In another embodiment of the first aspect, identifying the first set of cleaning products based on the health issues of occupants of the building and the ingredients of the plurality of cleaning products includes determining that an occupant of the building has one of a respiratory system irritation condition, a skin irritation condition, and an eye irritation condition and eliminating any product in the plurality of products that contains methylisothiazolinone.

In another embodiment of the first aspect, identifying the first set of cleaning products based on the health issues of occupants of the building and the ingredients of the plurality of cleaning products includes determining that an occupant of the building has one of a respiratory system irritation condition, a skin irritation condition, and an eye irritation condition and eliminating any product in the plurality of products that contains ammonium hydroxide.

In another embodiment of the first aspect the items that require cleaning in the building includes marble, where identifying the plurality of cleaning products for cleaning the items that require cleaning in the building includes identifying products that do not contain vinegar or lemon.

In another embodiment of the first aspect the items that require cleaning in the building includes granite, where identifying the plurality of cleaning products for cleaning the items that require cleaning in the building includes identifying products that do not contain bleach, vinegar, lemon, and hydrogen peroxide.

In a second aspect, a non-transitory computer-readable memory storing a program which when executed by a processor of a server provides health security for cleaning a building is provided. The program includes a set of instructions for receiving a request from a first electronic device for cleaning a building. The request includes a time and a date of cleaning, a set of one or more health issues of occupants of the building, and an identification of items that require cleaning in the building. The program includes a set of instructions for identifying a plurality of cleaning products for cleaning the items that require cleaning in the building. The program includes a set of instructions for identifying chemical ingredients of the plurality of cleaning products. The program includes a set of instructions for identifying a first set of one or more cleaning products in the plurality of cleaning products for cleaning of the building based on the health issues of occupants of the building and the chemical ingredients of the plurality of cleaning products. The program includes a set of instructions for providing the time and date, an identification of the building, and the identification of the first set of one or more cleaning products to electronic devices of a plurality of janitorial workers. The program includes a set of instructions for receiving a request from a second electronic device in the electronic devices of the plurality of janitorial workers to clean the building using the first set of cleaning products at the time and date of cleaning. The program includes a set of instructions for sending, a threshold time before the time and date of cleaning, a request to the second electronic device to turn on geolocation tracking, enable a camera of the second electronic device, and take geolocated images of a second set of cleaning products carried by the janitorial worker. The program includes a set of instructions for receiving, from the second electronic device, a set of one or more geolocated images of the second set of cleaning products. The program includes a set of instructions for analyzing the set of one or more geolocated images. The program includes a set of instructions for determining, based on the analysis, that the second electronic device is within a threshold distance of the building and the second set of cleaning products match the first set of products. The program includes a set of instructions for providing a clearance to the janitorial worker to perform the cleaning of the building based on the determination.

In an embodiment of the second aspect, the program further includes a set of instructions for receiving, from the second electronic device, ATP measurements made by a microbial detection sensor on a first surface in the building measurements. The program further includes a set of instructions for selecting, by the processor of the server, at least one cleaning product in the first set of one or more cleaning products to clean the first surface based on the ATP measurements. The program further includes a set of instructions for sending, by the processor of the server, an instruction to the person associated with the second electronic device to use the at least one product on the first surface.

In another embodiment of the second aspect, the program further includes a set of instructions for receiving, from the second electronic device, ATP measurements made by a microbial detection sensor on a first surface in the building measurements. The program further includes a set of instructions for selecting one or more cleaning products in the first set of one or more cleaning products to clean the first surface based on the ATP measurements. The program further includes a set of instructions for updating a profile of a user of the first client device to recommend the use of the one or more cleaning products for cleaning the first surface in furfure cleaning jobs of the building.

In another embodiment of the second aspect, the set of instructions for identifying the first set of one or more cleaning products in the plurality of cleaning products for cleaning of the building includes sets of instructions for receiving a range of temperature predictions at the time and date of cleaning from a weather information database and identifying the first set of one or more cleaning products from cleaning products that are recommended to work well in the predicted range of temperature at the time and date of cleaning.

While the invention has been described with reference to numerous specific details, one of ordinary skill in the art will recognize that the invention may be embodied in other specific forms without departing from the spirit of the invention. In addition, a number of the figures conceptually illustrate processes. The specific operations of these processes may not be performed in the exact order shown and described. The specific operations may not be performed in one continuous series of operations, and different specific operations may be performed in different embodiments. Furthermore, the process could be implemented using several sub-processes, or as part of a larger macro process.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. An automated method of providing health security for cleaning a building, the method comprising:

by a processor of a server, receiving a request from a first electronic device for cleaning a building, the request comprising a time and a date of cleaning, a set of one or more health issues of occupants of the building, and an identification of items that require cleaning in the building, an identification of a first set of cleaning products to be avoided at the building, and an identification of a second set of cleaning products requested by the first electronic device;

by the processor of the server, identifying a plurality of cleaning products for cleaning the items that require cleaning in the building;

by the processor of the server, identifying a plurality of chemical ingredients of the plurality of cleaning products by searching a cleaning products' chemical ingredient database for the chemical ingredients associated with the plurality of cleaning products;

by the processor of the server, identifying a third set of one or more cleaning products in the plurality of cleaning products for cleaning of the building based on the health issues of occupants of the building and the chemical ingredients of the plurality of cleaning products, wherein identifying the third set of one or more cleaning products comprises excluding the first set of cleaning products that are to be avoided at the building and including the requested second set of cleaning products;

by the processor of the server, providing the time and date, an identification of the building, and the identification of the third set of one or more cleaning products to electronic devices of a plurality of janitorial workers;

by the processor of the server, receiving a request from a second electronic device in the electronic devices of the plurality of janitorial workers to clean the building using the first third set of cleaning products at the time and date of cleaning;

by the processor of the server, a threshold time before the time and date of cleaning, sending a request to the second electronic device to (i) turn on geolocation tracking and (ii) when the second electronic device is within a geofence defining a threshold distance of the building, enable a camera of the second electronic device, and take a set of one or more geotagged images of a fourth set of cleaning products carried by the janitorial worker;

by the processor of the server, receiving, from the second electronic device, a set of one or more geotagged images of labels of the fourth set of cleaning products;

by the processor of the server, determining, based on the geotags of the geotagged images, whether the set of one or more geotagged images were captured within the threshold distance of the building;

when the set of one or more geotagged images were captured within the threshold distance of the building, by the processor of the server, identifying, from the images of the labels of the fourth set of cleaning products, names of the cleaning products in the fourth set of cleaning products;

when the set of one or more geotagged images were not captured within the threshold distance of the building, returning to the step of receiving, from the second electronic device, a set of one or more geotagged images of labels of the fourth set of cleaning products;

by the processor of the server, identifying chemical ingredients associated with the fourth set of cleaning products, by at least one of (i) identifying, from the images of the labels in the set of one or more geotagged images, the chemical ingredients listed on the labels, or (ii) searching a cleaning products' chemical ingredient database for the chemical ingredients associated with the names of the cleaning products in the fourth set of cleaning products;

by the processor of the server, determining whether the fourth set of cleaning products are included in the third set of one or more cleaning products, and that the cleaning products in the fourth set of cleaning products include the requested second set of cleaning products, and are not among the first set of cleaning products to be avoided at the building;

when the fourth set of cleaning products is not included in the third set of one or more cleaning products, or when the cleaning products in the fourth set of cleaning products do not include the requested second set of cleaning products, sending a message to the second electronic device indicating that the products carried by the janitorial worker are not proper for the cleaning job and withholding the clearance; and when (i) the set of one or more geotagged images were captured within the threshold distance of the building and (ii) the fourth set of cleaning products are included in the third set of one or more cleaning products and include the requested second set of cleaning products, providing, by the processor of the server, a clearance to the janitorial worker to perform the cleaning of the building.

2. The automated method of claim 1 further comprising:

receiving, by the processor of the server, from the second electronic device, adenosine triphosphate (ATP) measurements made by a microbial detection sensor on a first surface in the building;

selecting, by the processor of the server, at least one cleaning product in the third set of one or more cleaning products to clean the first surface based on the ATP measurements; and sending, by the processor of the server, an instruction to the person associated with the second electronic device to use the at least one product on the first surface.

3. The automated method of claim 1 further comprising:

receiving, by the processor of the server, from the second electronic device, adenosine triphosphate (ATP) measurements made by a microbial detection sensor on a first surface in the building;

selecting, by the processor of the server, one or more cleaning products in the third set of one or more cleaning products to clean the first surface based on the ATP measurements; and updating a profile of a user of the first electronic device to recommend the use of the one or more cleaning products for cleaning the first surface in future cleaning jobs of the building.

4. The automated method of claim 1 further comprising:

receiving cleaning product preferences from the first electronic device; and updating a profile of a user of the first electronic device, by the processor of the server, based on the received product preferences, wherein identifying a third set of one or more cleaning products in the plurality of cleaning products for cleaning of the building further comprises identifying the third set of one or more cleaning products based on the cleaning product preferences in the profile of the user of the first electronic device.

5. The automated method of claim 1, wherein identifying the third set of one or more cleaning products in the plurality of cleaning products for cleaning of the building comprises:

receiving, by the processor of the server, a range of temperature predictions at the time and date of cleaning from a weather information database; and identifying the third set of one or more cleaning products from cleaning products that are recommended to work well in the predicted range of temperature at the time and date of cleaning.

6. The automated method of claim 1, wherein identifying the third set of one or more cleaning products in the plurality of cleaning products for cleaning of the building further comprises:

receiving, by the processor of the server, precipitation predictions at the time and date of cleaning from a weather information database; and identifying the third set of one or more cleaning products from cleaning products that are recommended to work well for the predicted precipitation at the time and date of cleaning.

7. The automated method of claim 1, wherein identifying the third set of one or more cleaning products in the plurality of cleaning products for cleaning of the building further comprises:

receiving, by the processor of the server, precipitation predictions at the time and date of cleaning from a weather information database; and identifying the third set of one or more cleaning products from cleaning products that have less environmental impact in the predicted precipitation.

8. The automated method of claim 1, wherein identifying the third set of one or more cleaning products in the plurality of cleaning products for cleaning of the building further comprises:

receiving, by the processor of the server, humidity predictions at the time and date of cleaning from a weather information database; and

identifying the third set of one or more cleaning products from cleaning products based on the humidity predictions at the time and date of cleaning.

9. The automated method of claim 1 further comprising:

providing a plurality of time and date recommendations for cleaning of the building, by the processor of the server, based on information regarding precipitations and upcoming weather events in the region where the building is located; and receiving the time and the date for cleaning of the building from the first electronic device based on the plurality of time and date recommendations.

10. The automated method of claim 1 further comprising:

providing a plurality of time and date recommendations for cleaning of the building, by the processor of the server, based on peak energy consumption times received from an environmental information database; and receiving the time and the date for cleaning of the building from the first electronic device based on the plurality of time and date recommendations.

11. The automated method of claim 1, wherein identifying the third set of cleaning products based on the health issues of occupants of the building and the ingredients of the plurality of cleaning products comprises:

determining that an occupant of the building has asthma;

based on the determination:

eliminating any product in the plurality of products that contains phthalates; and eliminating any product in the plurality of products that contains Quaternary ammonia compounds (QUATS).

12. The automated method of claim 1, wherein identifying the third set of cleaning products based on the health issues of occupants of the building and the ingredients of the plurality of cleaning products comprises:

determining that an occupant of the building has one of a respiratory system irritation condition, a skin irritation condition, and an eye irritation condition;

based on the determination:

eliminating any product in the plurality of products that contains methylisothiazolinone; and eliminating any product in the plurality of products that contains ammonium hydroxide.

13. The automated method of claim 1, wherein the items that require cleaning in the building comprise marble, wherein identifying the plurality of cleaning products for cleaning the items that require cleaning in the building comprises identifying products that do not contain vinegar or lemon.

14. The automated method of claim 1, wherein the items that require cleaning in the building comprise granite, wherein identifying the plurality of cleaning products for cleaning the items that require cleaning in the building comprises identifying products that do not contain bleach, vinegar, lemon, and hydrogen peroxide.

15. The automated method of claim 1 further comprising:

after providing the clearance, sending a request to the second electronic device to capture and transmit an image of the janitorial worker once the cleaning job is complete and the janitorial worker is outside the building.

16. A non-transitory computer-readable memory storing a program which when executed by a processor of a server provides health security for cleaning a building, the program comprising sets of instructions for:

receiving a request from a first electronic device for cleaning a building, the request comprising a time and a date of cleaning, a set of one or more health issues of occupants of the building, an identification of items that require cleaning in the building, an identification of a first set of cleaning products to be avoided at the building, and an identification of a second set of cleaning products requested by the first electronic device;

identifying a plurality of cleaning products for cleaning the items that require cleaning in the building;

identifying a plurality of chemical ingredients of the plurality of cleaning products by searching a cleaning products' chemical ingredient database for the chemical ingredients associated with the plurality of cleaning products;

identifying a third set of one or more cleaning products in the plurality of cleaning products for cleaning of the building based on the health issues of occupants of the building and the chemical ingredients of the plurality of cleaning products, wherein identifying the third set of one or more cleaning products comprises excluding the first set of cleaning products that are to be avoided at the building and including the requested second set of cleaning products;

providing the time and date, an identification of the building, and the identification of the third set of one or more cleaning products to electronic devices of a plurality of janitorial workers;

receiving a request from a second electronic device in the electronic devices of the plurality of janitorial workers to clean the building using the third set of cleaning products at the time and date of cleaning;

a threshold time before the time and date of cleaning, sending a request to the second electronic device to (i) turn on geolocation tracking and (ii) when the second electronic device is within a geofence defining a threshold distance of the building, enable a camera of the second electronic device, and take a set of one or more geotagged images of a fourth set of cleaning products carried by the janitorial worker;

receiving, from the second electronic device, a set of one or more geotagged images of labels of the fourth set of cleaning products;

determining, based on the geotags of the geotagged images, whether the set of one or more geotagged images were captured within the threshold distance of the building;

when the set of one or more geotagged images were captured within the threshold distance of the building, identifying, from the images of the labels of the fourth set of cleaning products, names of the cleaning products in the fourth set of cleaning products;

when the set of one or more geotagged images were not captured within the threshold distance of the building, returning to the step of receiving, from the second electronic device, a set of one or more geotagged images of labels of the fourth set of cleaning products;

identifying chemical ingredients associated with the fourth set of cleaning products, by at least one of (i) identifying, from the images of the labels in the set of one or more geotagged images, the chemical ingredients listed on the labels, or (ii) searching a cleaning products' chemical ingredient database for the chemical ingredients associated with the names of the cleaning products in the fourth set of cleaning products;

determining whether the fourth set of cleaning products are included in the third set of one or more cleaning products, and that the cleaning products in the fourth set of cleaning products include the requested second set of cleaning products, and are not among the first set of cleaning products to be avoided at the building;

when the fourth set of cleaning products is not included in the third set of one or more cleaning products, or when the cleaning products in the fourth set of cleaning products do not include the requested second set of cleaning products, sending a message to the second electronic device indicating that the products carried by the janitorial worker are not proper for the cleaning job and withholding the clearance; and when (i) the set of one or more geotagged images were captured within the threshold distance of the building and (ii) the fourth set of cleaning products are included in the third set of one or more cleaning products and include the requested second set of cleaning products, providing a clearance to the janitorial worker to perform the cleaning of the building.

17. The non-transitory computer-readable memory of claim 16, the program further comprising sets of instructions for:

receiving, from the second electronic device, adenosine triphosphate (ATP) measurements made by a microbial detection sensor on a first surface in the building;

selecting, by the processor of the server, at least one cleaning product in the third set of one or more cleaning products to clean the first surface based on the ATP measurements; and sending, by the processor of the server, an instruction to the person associated with the second electronic device to use the at least one product on the first surface.

18. The non-transitory computer-readable memory of claim 16, the program further comprising sets of instructions for:

receiving, from the second electronic device, adenosine triphosphate (ATP) measurements made by a microbial detection sensor on a first surface in the building;

selecting one or more cleaning products in the third set of one or more cleaning products to clean the first surface based on the ATP measurements; and updating a profile of a user of the first electronic device to recommend the use of the one or more cleaning products for cleaning the first surface in future cleaning jobs of the building.

19. The non-transitory computer-readable memory of claim 16, wherein the set of instructions for identifying the third set of one or more cleaning products in the plurality of cleaning products for cleaning of the building comprises sets of instructions for:

receiving a range of temperature predictions at the time and date of cleaning from a weather information database; and identifying the third set of one or more cleaning products from cleaning products that are recommended to work well in the predicted range of temperature at the time and date of cleaning.

20. The non-transitory computer-readable memory of claim 16, the program further comprising sets of instructions for:

after providing the clearance, sending a request to the second electronic device to capture and transmit an image of the janitorial worker once the cleaning job is complete and the janitorial worker is outside the building.

* * * * *